United States Patent [19]

Kawahara et al.

[11] Patent Number: 5,750,762

[45] Date of Patent: May 12, 1998

[54] CYCLOPENTADIENE DERIVATIVE COMPOUNDS AND ELECTROPHOTOGRAPHIC PHOTOCONDUCTOR COMPRISING ONE CYCLOPENTADIENE DERIVATIVE COMPOUND

[75] Inventors: Megumi Kawahara, Yokohama; Ikuko Yamada, Kawasaki; Masayuki Shoshi, Yokohama; Akio Kojima, Mitaka, all of Japan

[73] Assignee: Ricoh Company, Ltd., Tokyo, Japan

[21] Appl. No.: 615,063

[22] Filed: Mar. 13, 1996

Related U.S. Application Data

[62] Division of Ser. No. 398,944, Mar. 2, 1995, Pat. No. 5,700,614.

[51] Int. Cl.$^6$ .................................................. C07C 255/07
[52] U.S. Cl. .......................................................... 558/423
[58] Field of Search ................................................ 558/423

[56] References Cited

U.S. PATENT DOCUMENTS

| | | | |
|---|---|---|---|
| 5,103,038 | 4/1992 | Chen et al. | 558/426 |
| 5,578,405 | 11/1996 | Ikegami et al. | 430/59 |

*Primary Examiner*—Johann Richter
*Assistant Examiner*—Ebenezer Sackey
*Attorney, Agent, or Firm*—Oblon, Spivak, McClelland, Maier & Neustadt, P.C.

[57] ABSTRACT

Cycolpentadiene derivative compounds, and an electrophotographic photoconductor comprising one cyclopentadiene derivative compound are disclosed. The cyclopentadiene derivative compounds are novel and useful for use in a photoconductive layer, and readily soluble in a binder resin. The electrophotographic photoconductor can be prepared by using a simple, effective production method. The electrophotographic photoconductor comprising one cyclopentadiene derivative compound provides a good light sensitivity and high durability.

6 Claims, 5 Drawing Sheets

CYCLOPENTADIENE DERIVATIVE COMPOUNDS AND ELECTROPHOTOGRAPHIC PHOTOCONDUCTOR COMPRISING ONE CYCLOPENTADIENE DERIVATIVE COMPOUND

This is a Division of application Ser. No. 08/398,944 filed on Mar. 2, 1995, now U.S. Pat. No. 5,700,614.

BACKGROUND OF THE INVENTION

The present invention generally relates to acceptor compounds and an electrophotographic photoconductor comprising one acceptor compound, and more particularly to cyclopentadiene derivative compounds and an electrophotographic photoconductor comprising one cyclopentadiene derivative compound in a photoconductive layer thereof, which is suitably applied to photoconductors of electrophotographic copiers and printers.

Inorganic photoconductive materials, such as selenium, selenium-tellurium alloy, and zinc oxide, have been widely applied to photoconductive layers of electrophotographic photoconductors. However, such materials are generally expensive, and the cost of manufacturing of the photoconductors was high. Therefore, it is desirable to realize an electrophotographic photoconductor which can be prepared from a less expensive source material but provide a good light-sensitive characteristic and high durability.

Recently, research and development of organic photoconductive materials for use in photoconductive layers of photoconductors of electrophotographic copiers and printers have made progress. Some of the electrophotographic photoconductors using the organic photoconductive materials are put into practical use. Most of such photoconductors include a photoconductive layer which has a laminated structure including a charge generating layer and a charge transporting layer. The charge transporting layer uses the organic photoconductive materials. The light sensitivity and the operating life of such photoconductors are different from those before considered, and have improved to a level equivalent to those of the inorganic materials mentioned above. The cost of manufacturing, the safety and the applicability of the above organic photoconductors are excellent even by comparison with those of the inorganic photoconductive materials.

The photoconductive layer of the electrophotographic photoconductors described above has a laminated structure including a charge generating layer and a charge transporting layer. The charger generating layer is made of a charge generating material, such as pigment or dye, on an electroconductive support. The charge transporting layer is made of a charge transporting material such as hydrazone or pyrazoline.

The charge transporting layer of the above electrophotographic photoconductor is a positive-hole transport type since the charge transporting material has an electron donative property. Thus, the photoconductor mentioned above has a light sensitivity which is effective only when the surface of the above photoconductors is negatively charged. However, a corona charge on the surface of the electrophotographic photoconductor when negatively charged is likely to be considerably unstable by comparison with a corona charge thereon when positively charged. A relatively great amount of ozone and NOx may be produced and they are absorbed by the electrophotographic photoconductors. Physical and chemical characteristics of the photoconductors are likely to deteriorate due to the ozone and NOx, and an environmental problem may arise because of the ozone and NOx.

Further, in order to carry out a development of an image on the negative-charged surface of the above electrophotographic photoconductor, it is necessary to use a positive-polarity toner with the electrophotographic photoconductor. However, it is generally difficult to produce a positive-polarity toner which is suitable for use with the above photoconductor. In a case of a two-component, high-resistance, magnetic-brush development method, it is found that a positive-charged type electrophotographic photoconductor used with a negative-polarity toner is more stable than the negative-charged type electrophotographic photoconductor used with the positive-polarity toner mentioned above. Also, it is found that the positive-charged type electrophotographic photoconductors provide a wider applicability and a greater degree of freedom of the working conditions thereof. For these reasons, the positive-charged type electrophotographic photoconductor used with the negative-polarity is considered advantageous and it provides a wider applicability.

A conventional electrophotographic photoconductor using an organic photoconductive material, such as 2,4,7-trinitro-9-fluorenone, the surface of which is positively charged for the development, has been proposed. This photoconductor has a laminated structure including a charge generating layer and a charge transporting layer on the charge generating layer. The ability of 2,4,7-trinitro-9-fluerenone to transport charge is found good. However, this charge transporting material has been found carcinogenic. Accordingly, the use of the electrophotographic photoconductors including the above charge transporting material in the electrophotographic copiers and printers might be harmful to health of human operators.

Some conventional compounds have been proposed for the charge transporting material mentioned above. For example, a fluorenilidene methane compound has been proposed in Japanese Laid-Open Patent Application No.60-69657, and an anthraquino-dimethane compound and anthrone derivatives have been proposed in Japanese Laid-Open Patent Application No.61-233750, for the above charge transporting materials. However, it is difficult for these compounds to realize a certain level of repeatability for image development of electrophotographic photoconductors in practical use.

In addition, a naphthalene-dicarboxylic acid imide compound and a naphthalene-tetracarboxylic acid diimide compound for the above charge transporting material have been proposed in Japanese Laid-Open Patent Application Nos.5-25136 and 5-25174, respectively. However, it is difficult for the above-mentioned compounds to realize a good light sensitivity of the electrophotographic photoconductors, and the solubility of these compounds in a binder resin is found low. It can be said that the above-mentioned compounds still have problems which remain unresolved.

U.S. Pat. No. 3,615,414 teaches a positive-charged type photoconductor including an eutectic complex of thiapyrilium salt (the charge generating material) and polycarbonate (the binder resin). However, it is difficult to prepare this photoconductor, and there is a problem that when image formation is repeated with the photoconductor a ghost image within a formed image on the photoconductor might appear.

Another positive-charged type electrophotographic photoconductor of conceivable use is a photoconductor which has a laminated structure including a charge generating layer as the upper layer and a charge transporting layer as the lower layer. The charge generating layer includes a charge generating material which generates positive holes or electrons when the photoconductor is illuminated by light from a light source. The charge transporting layer includes a charge transporting material which is capable of transporting the positive holes or electrons through the material. However, the electrophotographic photoconductor mentioned above has a problem in that the charge generating material in the upper layer is considerably affected by the environmental factors, such as ultraviolet rays, corona charge, humidity and mechanical friction, because the charge generating layer is very likely to be influenced by the environment factors on the surface of the electrophotographic photoconductor. The electrophotographic characteristics of the photoconductor mentioned above will deteriorate since the charge generator is affected by the environmental factors, and the quality of an image formed on the electrophotographic photoconductor will be lowered during warehouse storage or in the course of repeated image forming operations.

A known negative-charged type electrophotographic photoconductor has a laminated structure including a charge generating layer as the lower layer, a charge transporting layer as the middle layer, and a protective layer as the upper layer. In a case of this electrophotographic photoconductor, the protective layer and the charge transporting layer serve to protect the charge generating layer from being affected by the environmental factors so that the charge generating material included in the charge generating layer is hardly affected by the environmental factors.

In the case of the above-mentioned electrophotographic photoconductor, the protective layer is formed into a thin sheet of dielectric, transparent synthetic resin. However, the protective layer inherently serves to prevent the charge generating layer from being effectively illuminated by a light source. The light sensitivity of the above electrophotographic photoconductor is considerably lowered as the thickness of the protective layer increases.

As described in the foregoing, the conventional electrophotographic photoconductors have problems related to the light sensitivity, the durability and the working health. Thus, it is desirable to provide an electrophotographic photoconductor which provides a good light sensitivity and high durability by including a suitable acceptor compound therein.

SUMMARY OF THE INVENTION

Accordingly, it is a general object of the present invention to provide an improved electrophotographic photoconductor comprising a novel and useful acceptor compound in which the above-mentioned problems are eliminated.

Another object of the present invention is to provide an electrophotographic photoconductor comprising a charge-transport acceptor compound included in a photoconductive layer, which photoconductor provides a good light sensitivity and high durability.

Still another object of the present invention is to provide a novel charge-transport acceptor compound which is suitable for a photoconductive layer and is readily soluble with a binder resin, to allow for a simple, efficient production process of the electrophotographic photoconductor.

The above-mentioned object of the present invention is achieved by an electrophotographic photoconductor comprising an electroconductive support and a photoconductive layer formed thereon comprising as an effective component at least one cyclopentadiene derivative compound represented by formula [I]:

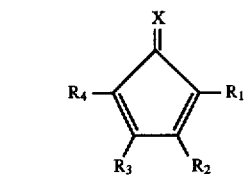

wherein $R_1$ and $R_4$ independently represent a hydrogen atom, a halogen atom, a cyano group, a nitro group, an alkyl group which may have a substituent, an aromatic group which may have a substituent, a heterocyclic group which may have a substituent, an alkoxycarbonyl group which may have a substituent, a carbamoyl group which may have a substituent, or an acyl group which may have a substituent, wherein $R_2$ and $R_3$ independently represent a hydrogen atom, an alkyl group which may have a substituent, an aromatic group which may have a substituent, or a heterocyclic group which may have a substituent, wherein X represents: an oxygen atom =O; a substitution group of a formula =C—[A][B] wherein A and B independently represent a hydrogen atom, a halogen atom, a cyano group, an aromatic group which may have a substituent, or a group —$COOR_6$ wherein $R_6$ represents an alkyl group which may have a substituent, or an aromatic group which may have a substituent; or a substitution group of a formula =N—$R_5$ wherein $R_5$ represents a cyano group, an alkyl group which may have a substituent, or an aromatic group which may have a substituent.

The above-mentioned object of the present invention is achieved by an electrophotographic photoconductor including an electroconductive support and a photoconductive layer formed thereon comprising as an effective component at least one cyclopentadiene derivative component represented by a formula:

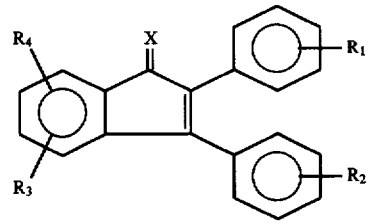

wherein $R_1$, $R_2$, $R_3$ and $R_4$ independently represent a hydrogen atom, a halogen atom, a cyano group, a nitro group, or an alkyl group which may have a substituent, wherein X represents: an oxygen atom =O; a substitution group of a formula =C—[A][B] wherein A and B independently represent a hydrogen atom, a halogen atom, a cyano group, an aromatic group which may have a substituent, or a group —$COOR_6$ wherein $R_6$ represents an alkyl group which may have a substituent, or an aromatic group which may have a substituent; or a substitution group of a formula =N—$R_5$ where $R_5$ represents a cyano group, an alkyl group which may have a substituent, or an aromatic group which may have a substituent.

The above-mentioned object of the present invention is achieved by a cyclopentadiene derivative compound of formula [I]:

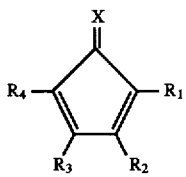

wherein $R_1$ and $R_4$ independently represent a hydrogen atom, a halogen atom, a cyano group, a nitro group, an alkyl group which may have a substituent, an aromatic group which may have a substituent, a heterocyclic group which may have a substituent, an alkoxycarbonyl group which may have a substituent, a carbamoyl group which may have a substituent, or an acyl group which may have a substituent, wherein $R_2$ and $R_3$ independently represent a hydrogen atom, an alkyl group which may have a substituent, an aromatic group which may have a substituent, or a heterocyclic group which may have a substituent, wherein X represents: an oxygen atom =O; a substitution group of a formula =C—[A][B] wherein A and B independently represent a hydrogen atom, a halogen atom, a cyano group, an aromatic group which may have a substituent, or a group —$COOR_6$ wherein $R_6$ represents an alkyl group which may have a substituent, or an aromatic group which may have a substituent; or a substitution group of a formula =N—$R_5$ wherein $R_5$ represents a cyano group, an alkyl group which may have a substituent, or an aromatic group which may have a substituent.

The above-mentioned object of the present invention is achieved by a cyclopentadiene derivative compound of a formula:

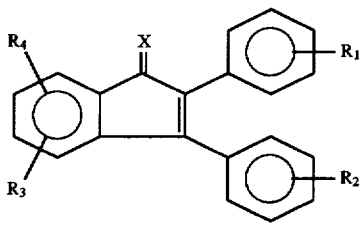

wherein $R_1$, $R_2$, $R_3$ and $R_4$ independently represent a hydrogen atom, a halogen atom, a cyano group, a nitro group, or an alkyl group which may have a substituent, wherein X represents: an oxygen atom =O; a substitution group of a formula =C—[A][B] wherein A and B independently represent a hydrogen atom, a halogen atom, a cyano group, an aromatic group which may have a substituent, or a group —$COOR_6$ wherein $R_6$ represents an alkyl group which may have a substituent, or an aromatic group which may have a substituent; or a substitution group of a formula =N—$R_5$ where $R_5$ represents a cyano group, an alkyl group which may have a substituent, or an aromatic group which may have a substituent.

The cyclopentadiene derivative compounds according to the present invention can be prepared through a simple, efficient production method. The acceptor compounds of the present invention are readily solved in a binder resin, and they have excellent charge acceptance and charge transport abilities, and provide an excellent charge transporting function by including them in the photoconductive layer. Evaluation tests have verified that the electrophotographic photoconductor comprising one cyclopentadiene derivative compound of the present invention provides a good light sensitivity and high durability.

BRIEF DESCRIPTION OF THE DRAWINGS

Other objects, features and advantages of the present invention will be more apparent from the following detailed description when read in conjunction with the accompanying drawings in which.

DESCRIPTION OF THE PREFERRED EMBODIMENTS

Figure 1:
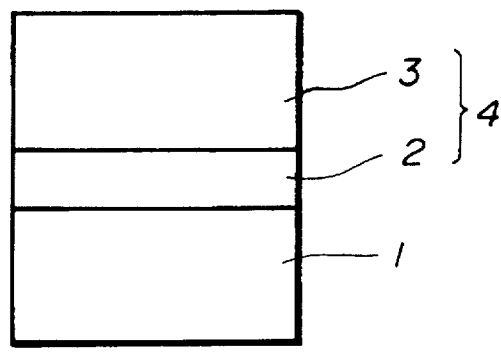
FIG. 1 is a cross-sectional view of an electrophotographic photoconductor having a construction of layers in one embodiment of the present invention.

A description will now be given of an electrophotographic photoconductor comprising a cyclopentadiene derivative compound in one embodiment of the present invention.

The acceptor compound in one embodiment of the present invention is a cyclopentadiene derivative compound, and this compound consists of a composition represented by formula [I]:

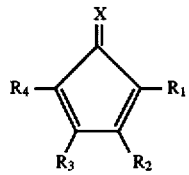

wherein $R_1$ and $R_4$ independently represent a hydrogen atom, a halogen atom, a cyano group, a nitro group, an alkyl group which may have a substituent, an aromatic group which may have a substituent, a heterocyclic group which may have a substituent, an alkoxycarbonyl group which may have a substituent, phenoxycarbonyl, a carbamoyl group which may have a substituent, or an acyl group which may have a substituent, wherein $R_2$ and $R_3$ independently represent a hydrogen atom, an alkyl group which may have a substituent, an aromatic group which may have a substituent, or a heterocyclic group which may have a substituent, wherein $R_3$ and $R_4$ may represent a phenyl group which may have a substituent, said phenyl group being formed integrally with said cyclopentadiene compound, wherein X represents:
an oxygen atom =O;
a substitution group of a formula =C—[A][B] wherein A and B independently represent a hydrogen atom, a halogen atom, a cyano group, an aromatic group which may have a substituent, or a group —$COOR_6$ wherein $R_6$ represents an alkyl group which may have a substituent, or an aromatic group which may have a substituent; or a substitution group of a formula =N—R₅ wherein R₅ represents a cyano group, an alkyl group which may have a substituent, or an aromatic group which may have a substituent.

Specific examples of the substituents related to the above formula [I] will be given below.

The alkyl group for each of $R_1$ and $R_4$ in the above formula [I] is one from among groups including methyl, ethyl, isopropyl, t-butyl, n-butyl, hexyl, octyl, one of cycloalkyl groups, such as cyclohexyl and cyclopentyl, one of halogen alkyl groups, such as trifluoromethyl, chloromethyl, bromoethyl and fluoropropyl, and one of benzyl groups.

The aromatic group for each of $R_1$ and $R_4$ in the above formula [I] is one from among groups including phenyl, naphthyl, anthracene, and pyrene. Examples of the substituent of a hydrogen atom in the aromatic group mentioned above are: chloro, bromo, methyl, ethyl, isopropyl, t-butyl, n-butyl, nitro, cyano, methoxyl, ethoxyl, acetoxyl, methoxycarbonyl, ethoxycarbonyl, buthoxycarbonyl, methylcarbonyl, ethylcarbonyl, N,N-dimethylamino, benzoxyamino, N,N-dimethylamido, methylthioxy, trifluoromethyl, and phenyl.

The heterocyclic group for each of $R_1$ and $R_4$ in the above formula [I] is one from among groups including furan, thiophene, pyridine, benzofuran, quinoxaline, and piperazine. Examples of the substituents in the above heterocyclic group are: methyl, ethyl, isopropyl, t-butyl, n-butyl, chloro, bromo, nitro, cyano, and methoxycarbonyl.

The alkoxycarbonyl group for each of $R_1$ and $R_4$ in the above formula [I] is one from among methoxycarbonyl, ethoxycarbonyl, butoxycarbonyl, and 3-chlorobutoxycarbonyl.

The carbamoyl group for each of $R_1$ and $R_4$ in the above formula [I] is one from among N,N-dimethylcarbamoyl, N,N-dihexylcarbamoyl, N-ethylcarbamoyl, and N,N-ditolylcarbamoyl.

The acyl group for each of $R_1$ and $R_4$ in the above formula [I] is one from among methylcarbonyl, ethylcarbonyl, hexylcarbonyl, and tolylcarbonyl.

The halogen atom for each of $R_1$ and $R_4$ in the above formula [I] is one from among fluorine, chlorine, bromine, and iodine.

The alkyl group, the aromatic group, and the heterocyclic group for each of $R_2$ and $R_3$ in the above formula [I] are the same as those for each of $R_1$ and $R_4$ in the above formula [I].

The aromatic group for each of A and B in the formula =C—[A][B] is the same as that for each of $R_1$ and $R_4$ in the above formula [I].

The alkyl group and the aromatic group for each of $R_5$ and $R_6$ are the same as those for each of $R_1$ and $R_4$ in the above formula [I].

Examples of the cyclopentadiene derivative compounds in various embodiments of the present invention, each consisting of the composition represented by the above formula [I], are listed in TABLES 1 through 12 which follows. However, the present invention is not limited to these examples only.

TABLE 1

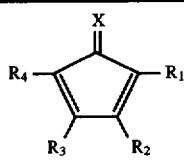

| COMPOUND NO. | X | $R_1$ | $R_2$ | $R_3$ | $R_4$ |
|---|---|---|---|---|---|
| 1 | =O | phenyl | phenyl | phenyl | phenyl |
| 2 | =C(CN)(COOC₄H₉) | phenyl | phenyl | phenyl | phenyl |
| 3 | =C(CN)(CN) | phenyl | phenyl | phenyl | phenyl |
| 4 | =N—CN | 4-Cl-phenyl | phenyl | phenyl | 4-Cl-phenyl |
| 5 | =N-phenyl-CH(CH₃)₂ | 4-NO₂-phenyl | phenyl | phenyl | 4-NO₂-phenyl |

TABLE 1-continued

Structure: cyclopentadienone-type with X at top, R₄ and R₁ on upper carbons, R₃ and R₂ on lower carbons.

| COMPOUND NO. | X | R₁ | R₂ | R₃ | R₄ |
|---|---|---|---|---|---|
| 6 | =C(CH(CH₃)₂)(2-methylphenyl) | phenyl-OCH₃ | phenyl | phenyl | phenyl-OCH₃ |
| 7 | =C(4-cyanophenyl)(4-cyanophenyl) | phenyl-OCOCH₃ | phenyl | phenyl | phenyl-OCOCH₃ |
| 8 | =C(CN)(2-methylphenyl) | phenyl-OC₂H₅ | phenyl | phenyl | phenyl-OC₂H₅ |
| 9 | =C(COOC₂H₆)(COOC₂H₆) | phenyl-COC₂H₆ | phenyl | phenyl | phenyl-COC₂H₆ |
| 10 | =O | phenyl-COOC₄H₉ | phenyl-F | phenyl-F | phenyl-COOC₄H₉ |

TABLE 2

| COMPOUND NO. | X | R₁ | R₂ | R₃ | R₄ |
|---|---|---|---|---|---|
| 11 | =C(CN)(COOC₃H₇) | phenyl-COCH₃ | phenyl-Cl | phenyl-Cl | phenyl-COCH₃ |
| 12 | =N-(2,6-diethylphenyl) | phenyl-N(CH₃)₂ | 2-furyl | 2-furyl | phenyl-N(CH₃)₂ |
| 13 | =C(CN)(3-cyanophenyl) | phenyl-CON(CH₃)₂ | 2-chlorophenyl | 3,4-dimethoxyphenyl | phenyl-CON(CH₃)₂ |

TABLE 2-continued

| COMPOUND NO. | X | $R_1$ | $R_2$ | $R_3$ | $R_4$ |
|---|---|---|---|---|---|
| 14 | =C(CN)(3-NO$_2$-C$_6$H$_4$) | -C$_6$H$_5$ | -C$_6$H$_4$-SCH$_3$ | -C$_6$H$_4$-SCH$_3$ | -C$_6$H$_5$ |
| 15 | =C(CN)(naphthyl) | -C$_6$H$_5$ | 3,4-methylenedioxyphenyl | 3,4-methylenedioxyphenyl | -C$_6$H$_5$ |
| 16 | =C(CN)(2-Cl-C$_6$H$_4$) | -C$_6$H$_5$ | 3,4,5-(OCH$_3$)$_3$-C$_6$H$_2$ | 3,4,5-(OCH$_3$)$_3$-C$_6$H$_2$ | -C$_6$H$_5$ |
| 17 | =C(CN)(2-OCH$_3$-C$_6$H$_4$) | -C$_6$H$_4$-NHCO-C$_6$H$_5$ | -C$_6$H$_4$-C(CH$_3$)$_3$ | -C$_6$H$_4$-C(CH$_3$)$_3$ | -C$_6$H$_4$-NHCO-C$_6$H$_5$ |
| 18 | =O | -C$_6$H$_5$ | -C$_6$H$_4$-CH$_3$ | -C$_6$H$_4$-CH$_3$ | -C$_6$H$_5$ |
| 19 | =C(CN)(COOC$_4$H$_9$) | -C$_6$H$_5$ | -C$_6$H$_4$-CH$_3$ | -C$_6$H$_4$-CH$_3$ | -C$_6$H$_5$ |

TABLE 3

| COMPOUND NO. | X | $R_1$ | $R_2$ | $R_3$ | $R_4$ |
|---|---|---|---|---|---|
| 20 | =C(CN)$_2$ | -C$_6$H$_4$-CH$_3$ | -C$_6$H$_4$-C$_2$H$_5$ | -C$_6$H$_4$-C$_2$H$_5$ | -C$_6$H$_4$-CH$_3$ |
| 21 | =N-CN | -C$_6$H$_4$-CN | -C$_6$H$_4$-CON(C$_2$H$_5$)$_2$ | -C$_6$H$_4$-CON(C$_2$H$_5$)$_2$ | -C$_6$H$_4$-CN |
| 22 | =O | -C$_6$H$_5$ | -C$_6$H$_4$-OCH$_3$ | -C$_6$H$_4$-OCH$_3$ | -C$_6$H$_5$ |
| 23 | =O | -C$_6$H$_5$ | -C$_6$H$_4$-OCH$_3$ | -C$_6$H$_4$-OCH$_3$ | -C$_6$H$_5$ |

TABLE 3-continued

| COMPOUND NO. | X | R₁ | R₂ | R₃ | R₄ |
|---|---|---|---|---|---|
| 24 | =N–C₆H₄(COCH₃) | C₆H₄(SCH₃) | C₆H₄(OCH₃) | C₆H₄(OCH₃) | C₆H₄(SCH₃) |
| 25 | =C(CN)(COOH) | C₆H₄(Br) | C₆H₅ | C₆H₅ | C₆H₄(Br) |
| 26 | =C(CN)(COOC₄H₉) | C₆H₅ | C₆H₄(OCH₃) | C₆H₄(OCH₃) | C₆H₅ |
| 27 | =C(CN)(COOC₄H₉) | C₆H₅ | C₆H₄(OCH₃) | C₆H₄(OCH₃) | C₆H₅ |
| 28 | =O | C₆H₅ | furyl | furyl | C₆H₅ |
| 29 | =C(CN)(COOC₄H₉) | C₆H₅ | benzodioxolyl | benzodioxolyl | C₆H₅ |

TABLE 4

| COMPOUND NO. | X | R₁ | R₂ | R₃ | R₄ |
|---|---|---|---|---|---|
| 30 | =C(CN)(COOC₈H₁₇) | C₆H₅ | C₆H₅ | C₆H₅ | C₆H₅ |
| 31 | =C(COOC₆H₁₃)(COOC₆H₁₃) | C₆H₅ | C₆H₅ | C₆H₅ | C₆H₅ |
| 32 | =O | C₆H₄(CH₃) | C₆H₅ | C₆H₅ | C₆H₄(CH₃) |
| 33 | =C(CN)(COOC₄H₉) | C₆H₄(C₂H₅) | C₆H₅ | C₆H₅ | C₆H₄(C₂H₅) |

TABLE 4-continued

| COMPOUND NO. | X | R₁ | R₂ | R₃ | R₄ |
|---|---|---|---|---|---|
| 34 | $=C\begin{smallmatrix}CN\\COOC_6H_{13}\end{smallmatrix}$ | -⌬-CH(CH₃)₂ | -⌬ | -⌬ | -⌬-CH(CH₃)₂ |
| 35 | =O | -⌬-C(CH₃)₃ | -⌬ | -⌬ | -⌬-C(CH₃)₃ |
| 36 | $=C\begin{smallmatrix}CN\\COOC_4H_9\end{smallmatrix}$ | -⌬(C₄H₉) | -⌬ | -⌬ | -⌬(C₄H₉) |
| 37 | $=C\begin{smallmatrix}CN\\COOC_8H_{17}\end{smallmatrix}$ | -⌬-CF₃ | -⌬ | -⌬ | -⌬-CF₃ |
| 38 | $=C\begin{smallmatrix}CN\\COOC_4H_9\end{smallmatrix}$ | -furan | -⌬ | -⌬ | -furan |
| 39 | =O | -COO-⌬ | -⌬ | -⌬ | -COO-⌬ |

TABLE 5

| COMPOUND NO. | X | R₁ | R₂ | R₃ | R₄ |
|---|---|---|---|---|---|
| 40 | =O | -COOC₄H₉ | -⌬ | -⌬ | -COOC₄H₉ |
| 41 | $=C\begin{smallmatrix}CN\\COOC_4H_9\end{smallmatrix}$ | $\begin{smallmatrix}C_2H_5\\|\\-CONH\end{smallmatrix}$ | -⌬ | -⌬ | $\begin{smallmatrix}C_2H_5\\|\\-CONH\end{smallmatrix}$ |
| 42 | =O | -⌬ | -⌬-COOCH₃ | -⌬-COOCH₃ | -⌬ |
| 43 | $=C\begin{smallmatrix}CN\\COOC_4H_9\end{smallmatrix}$ | -⌬ | -⌬-COOCH₃ | -⌬-COOCH₃ | -⌬ |
| 44 | $=C\begin{smallmatrix}CN\\CN\end{smallmatrix}$ | -⌬ | -⌬-COOCH₃ | -⌬-COOCH₃ | -⌬-COOCH₃ |
| 45 | =O | -⌬-COOCH₃ | -⌬-COOCH₃ | -⌬-COOCH₃ | -⌬-COOCH₃ |
| 46 | $=C\begin{smallmatrix}CN\\COOC_2H_5\end{smallmatrix}$ | -⌬-COOC₂H₅ | -⌬-COOC₂H₅ | -⌬-COOC₂H₅ | -⌬-COOC₂H₅ |

TABLE 5-continued

| COMPOUND NO. | X | R₁ | R₂ | R₃ | R₄ |
|---|---|---|---|---|---|
| 47 | =O | Ph | $-C_2H_5$ | $-C_2H_5$ | Ph |
| 48 | =C(CN)(COOC₄H₉) | Ph | $-C_2H_5$ | $-C_2H_5$ | Ph |
| 49 | =O | Ph | $-CH_3$ | $-CH_3$ | Ph |

TABLE 6

| COMPOUND NO. | X | R₁ | R₂ | R₃ | R₄ |
|---|---|---|---|---|---|
| 50 | =C(CN)(COOC₄H₉) | Ph | $-CH_3$ | $-CH_3$ | Ph |
| 51 | =C(CN)(CN) | Ph | $-CH_3$ | $-CH_3$ | Ph |
| 52 | =C(CN)(COOC₄H₉) | Ph-Br | $-CH_3$ | $-CH_3$ | Ph-Br |
| 53 | =O | $-C_2H_5$ | Ph | Ph | $-C_2H_5$ |
| 54 | =C(CN)(COOC₄H₉) | $-C_2H_5$ | Ph | Ph | $-C_2H_5$ |
| 55 | =O | $-CH_3$ | Ph | Ph | $-CH_3$ |
| 56 | =C(CN)(COOC₄H₉) | $-CH_3$ | Ph | Ph | $-CH_3$ |
| 57 | =C(CN)(CN) | $-CH_3$ | Ph | Ph | $-CH_3$ |
| 58 | =O | $-CH_3$ | Ph-COOCH₃ | Ph-COOCH₃ | $-CH_3$ |
| 59 | =C(CN)(COOC₂H₅) | $-CH_3$ | Ph-COOCH₃ | Ph-COOCH₃ | $-CH_3$ |

TABLE 7

| Compound No. | X | $R_1$ | $R_2$ | $R_3$ | $R_4$ |
|---|---|---|---|---|---|
| 60 | =C(CN)(CN) | —CH$_3$ | —C$_6$H$_4$—COOCH$_3$ | —C$_6$H$_4$—COOCH$_3$ | —CH$_3$ |
| 61 | =O | —CH$_3$ | —C$_6$H$_5$ | —C$_6$H$_5$ | —C$_6$H$_5$ |
| 62 | =C(CN)(COOC$_4$H$_9$) | —CH$_3$ | —C$_6$H$_5$ | —C$_6$H$_5$ | —C$_6$H$_5$ |
| 63 | =C(CN)(CN) | —CH$_3$ | —C$_6$H$_5$ | —C$_6$H$_5$ | —C$_6$H$_5$ |
| 64 | =O | —CH$_3$ | —C$_6$H$_4$—COOCH$_3$ | —C$_6$H$_4$—COOCH$_3$ | —C$_6$H$_5$ |
| 65 | =C(CN)(COOC$_2$H$_5$) | —CH$_3$ | —C$_6$H$_4$—COOCH$_3$ | —C$_6$H$_4$—COOCH$_3$ | —C$_6$H$_5$ |
| 66 | =C(CN)(CN) | —CH$_3$ | —C$_6$H$_4$—COOCH$_3$ | —C$_6$H$_4$—COOCH$_3$ | —C$_6$H$_5$ |
| 67 | =O | —C$_6$H$_5$ | —CH$_3$ | —C$_6$H$_5$ | —C$_6$H$_5$ |
| 68 | =C(CN)(COOC$_4$H$_9$) | —C$_6$H$_5$ | —CH$_3$ | —C$_6$H$_5$ | —C$_6$H$_5$ |
| 69 | =C(CN)(CN) | —C$_6$H$_5$ | —CH$_3$ | —C$_6$H$_5$ | —C$_6$H$_5$ |

TABLE 8

| Compound No. | X | $R_1$ | $R_2$ | $R_3$ | $R_4$ |
|---|---|---|---|---|---|
| 70 | =O | —C$_6$H$_4$—COOCH$_3$ | —CH$_3$ | —C$_6$H$_5$ | —C$_6$H$_4$—COOCH$_3$ |
| 71 | =C(CN)(COOC$_2$H$_5$) | —C$_6$H$_4$—COOCH$_3$ | —CH$_3$ | —C$_6$H$_5$ | —C$_6$H$_4$—COOCH$_3$ |

TABLE 8-continued

| COMPOUND NO. | X | R₁ | R₂ | R₃ | R₄ |
|---|---|---|---|---|---|
| 72 | $=C(CN)_2$ | Ph-COOCH₃ | —CH₃ | Ph | Ph-COOCH₃ |
| 73 | =O | —COOCH₃ | Ph | Ph | —COOCH₃ |
| 74 | $=C(CN)(COOC_2H_5)$ | —COOCH₃ | Ph | Ph | —COOCH₃ |
| 75 | $=C(CN)_2$ | —COOCH₃ | Ph | Ph | —COOCH₃ |
| 76 | =O | —COOC₂H₅ | Ph | Ph | —COOC₂H₅ |
| 77 | $=C(CN)(COOC_2H_5)$ | —COOC₂H₅ | Ph | Ph | —COOC₂H₅ |
| 78 | $=C(CN)_2$ | —COOC₂H₅ | Ph | Ph | —COOC₂H₅ |
| 79 | =O | —COOCH₃ | Ph-COOCH₃ | Ph-COOCH₃ | —COOCH₃ |

TABLE 9

| COMPOUND NO. | X | R₁ | R₂ | R₃ | R₄ |
|---|---|---|---|---|---|
| 80 | $=C(CN)(COOC_2H_5)$ | —COOCH₃ | Ph-COOCH₃ | Ph-COOCH₃ | —COOCH₃ |
| 81 | $=C(CN)_2$ | —COOCH₃ | Ph-COOCH₃ | Ph-COOCH₃ | —COOCH₃ |
| 82 | =O | —COC₂H₅ | Ph | Ph | —COC₂H₅ |
| 83 | $=C(CN)_2$ | —COC₆H₁₃ | Ph | Ph | —COC₆H₁₃ |

TABLE 9-continued

| COMPOUND NO. | X | R₁ | R₂ | R₃ | R₄ |
|---|---|---|---|---|---|
| 84 | =O | —Ph | —Ph | —CH₃ | —CH₃ |
| 85 | =O | —Ph | —CH₃ | —Ph | —CH₃ |
| 86 | =C(CN)(COOC₄H₉) | —Ph | —Ph | —CH₃ | —CH₃ |
| 87 | =C(CN)(CN) | —Ph | —Ph | —CH₃ | —CH₃ |
| 88 | =C(CN)(COOC₄H₉) | —Ph | —CH₃ | —Ph | —CH₃ |
| 89 | =C(CN)(CN) | —Ph | —CH₃ | —Ph | —CH₃ |

TABLE 10

| COMPOUND NO. | X | R₁ | R₂ | R₃ | R₄ |
|---|---|---|---|---|---|
| 90 | =O | —CON(CH₃)₂ | —Ph | —Ph | —CON(CH₃)₂ |
| 91 | =C(CN)(CN) | —CON(CH₃)₂ | —Ph | —Ph | —CON(C₆H₁₃)₂ |
| 92 | =O | —CN | —Ph | —Ph | —Ph |
| 93 | =C(CN)(COOC₄H₉) | —CN | —C₆H₄—C(CH₃)₃ | —C₆H₄—C(CH₃)₃ | —Ph |
| 94 | =O | —Br | —Ph | —Ph | —Ph |
| 95 | =O | —NO₂ | —C₆H₄—NO₂ | —C₆H₄—NO₂ | —Ph |

TABLE 10-continued

| COMPOUND NO. | X | R₁ | R₂ | R₃ | R₄ |
|---|---|---|---|---|---|
| 96 | =O | cyclohexyl-H | 2-methoxyphenyl (OCH₃) | 2-methoxyphenyl (OCH₃) | cyclohexyl-H |
| 97 | =N—C₄H₉ | naphthyl | phenyl | phenyl | naphthyl |
| 98 | =N—C₆H₄—CF₃ | C₆H₄—CF₃ | 3,4-methylenedioxyphenyl | 3,4-methylenedioxyphenyl | C₆H₄—CF₃ |
| 99 | =O | pyridyl (N) | phenyl | phenyl | pyridyl (N) |

TABLE 11

| COMPOUND NO. | X | R₁ | R₂ | R₃ | R₄ |
|---|---|---|---|---|---|
| 100 | =C(CN)(COOC₃H₇) | —CH₂CH₂F | C₆H₄—CON(CH₃)₂ | C₆H₄—CON(CH₃)₂ | —CH₂—CF₃ |
| 101 | =C(CN)₂ | —CH₂CH₃ | cyclohexyl-H | cyclohexyl-H | —CH₃ |
| 102 | =N—C₄H₉ | —CF₂CH₂Br | phenyl | phenyl | —CH₂CH₃ |
| 103 | =C(CN)₂ | —C₃H₇ | —C₃H₇ | —C₃H₇ | —C₃H₇ |
| 104 | =N—CN | —CH(CH₃)₂ | 3,4-methylenedioxyphenyl | 3,4-methylenedioxyphenyl | —CH(CH₃)₂ |
| 105 | =C(CN)(COO-phenyl) | —C(CH₃)₃ | 4-methylphenyl (CH₃) | 4-methylphenyl (CH₃) | —C(CH₃)₃ |

TABLE 11-continued

| COMPOUND NO. | X | R₁ | R₂ | R₃ | R₄ |
|---|---|---|---|---|---|
| 106 | =C(CN)(CN) | −C₄H₉ | naphthyl | naphthyl | −C₄H₉ |
| 107 | =C(CN)(CN) | −C₆H₁₃ | pyrenyl | pyrenyl | −C₆H₁₃ |
| 108 | =C(CN)(COOCH₃) | −C₈H₁₇ | −C₆H₄−COO−C₆H₅ | −C₆H₄−COO−C₆H₅ | −C₈H₁₇ |
| 109 | =C(CN)(2-Br-C₆H₄) | −C₆H₁₁ (H) | −C₆H₄−COCH₃ | −C₆H₄−COCH₃ | −C₆H₁₁ (H) |

TABLE 12

| COMPOUND NO. | X | R₁ | R₂ | R₃ | R₄ |
|---|---|---|---|---|---|
| 110 | =C(CN)(4-CF₃-C₆H₄) | −CF₃ | −C₆H₄−CON(CH₃)₂ | −C₆H₄−CON(CH₃)₂ | −CF₃ |
| 111 | =C(CN)(4-COCH₃-C₆H₄) | −CH₂−C₆H₅ | −CH₃ | −C₆H₅ | −CH₂−C₆H₅ |
| 112 | =C(CN)(CN) | anthracenyl | H | H | anthracenyl |
| 113 | =C(CN)(CN) | −C₆H₅ | −C₂H₅ | −C₂H₅ | −C₆H₅ |

The cyclopentadiene derivative compound, consisting of the composition represented by the above formula [I], is prepared through the following methods. In order to prepare the cyclopentadiene compound in one embodiment of the present invention, it is first necessary to obtain an intermediate pentadiene compound by reaction of a ketone compound and a diketone compound in the presence of a basic catalyst. This reaction is in accordance with the known Lewis acid-base concept. The intermediate pentadiene compound mentioned above is prepared by performing the reaction in accordance with formula [I']:

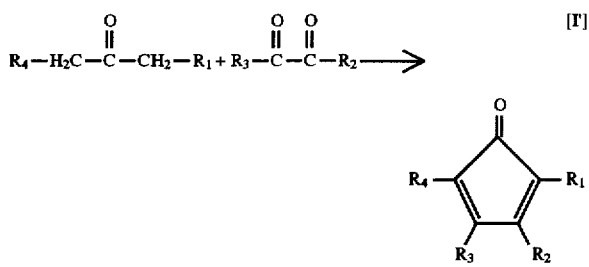

where $R_1$, $R_2$, $R_3$ and $R_4$ are the same as those in the above formula [I].

Examples of the basic catalyst mentioned above are: organic bases, such as N-methylmorpholine, N-methylpiperidine, pyridine, piperidine, and triethylamin; and inorganic bases, such as sodium acetate, potassium acetate, ammonium acetate, sodium carbonate, and potassium carbonate.

The reaction to prepare the intermediate penthadiene compound mentioned above is performed with or without a solvent at temperatures from normal temperature to 150° C., and preferably temperatures from normal temperature to 100° C. Examples of the solvent mentioned above are methyl alcohol, ethyl alcohol, isopropyl alcohol, butyl alcohol, acetic acid, tetrahydrofuran, 1,4-dioxane, N,N-dimethylformaldehyde, benzene, toluene, chlorobenzene, and xylene.

In order to prepare the cyclopentadiene compound in one embodiment of the present invention, it is secondly necessary to make the above intermediate penthadiene compound react with a third compound in the presence of an acid catalyst or basic catalyst.

The third compound mentioned above is represented by one of the following formulas:

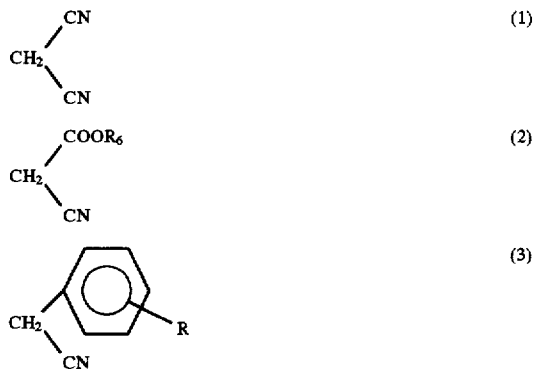

where $R_6$ is the same as $R_6$ in the above formula [I], and R is the same as $R_1$ in the above formula [I]. Examples of the above-mentioned third compound are: malononitrile represented by the formula (1); alkylcyanoacetate represented by the formula (2); allylacetonitrile represented by the formula (3); and dialkyl malonate represented by the formula (4).

Examples of the acid catalyst mentioned above are titanium tetrachloride, zinc chloride, aluminium chloride, and boron trifluoride. Examples of the basic catalyst mentioned above are N-methylmorpholine, N-methylpiperidine, pyridine, piperidine, triethylamin, sodium acetate, potassium acetate, ammonium acetate, sodium carbonate, and potassium carbonate.

The reaction to prepare the third compound mentioned above is performed with or without a solvent at temperatures from −20° C. to 150° C., and preferably temperatures from 0° C. to 100° C., in order to prepare the cyclopentadiene compound in one embodiment of the present invention. Examples of the solvent mentioned above are dichloromethane, dichloroethane, tetrahydrofuran, dioxane, benzen, and toluene.

Further, the cyclopentadiene compound in one embodiment of the present invention can be prepared by reaction of the above intermediate pentadiene compound and an aniline compound in the presence of an acid catalyst. The aniline compound mentioned above is represented by formula (5):

$$H_2N-R_5 \qquad (5)$$

where $R_5$ is the same as that in the above formula [I].
It is preferable to make use of the preparation process which is described here, when $R_5$ in the above formula (5) indicates a cyano group.

Examples of the acid catalyst mentioned above are titanium tetrachloride, zinc chloride, aluminium chloride, and boron trifluoride.

The reaction to prepare the aniline compound mentioned above is performed with or without a solvent at temperatures from −20° C. to 150° C., and preferably temperatures from 0° C. to 100° C. Examples of the solvent mentioned above are dichloromethane, dichloroethane, tetrahydrofuran, dioxane, benzen, and toluene.

Further, the cyclopentadiene compound in one embodiment of the present invention can be prepared by reaction of the above intermediate pentadiene compound and a diimide compound in the presence of an acid catalyst. The diimide compound mentioned above is represented by formula (6):

$$(CH_3)_3Si-N=C=N-Si(CH_3)_3 \qquad (6)$$

Examples of the acid catalyst mentioned above are titanium tetrachloride, zinc chloride, aluminium chloride, and boron trifluoride.

The reaction with the diimide compound mentioned above is performed with or without solvent at temperatures from −20° C. to 150° C., or preferably temperatures from 0° C. to 100° C., in order to prepare the cyclopentadiene compound in one embodiment of the present invention. Examples of the solvent mentioned above are dichloromethane, dichloroethane, tetrahydrofuran, dioxane, benzen, and toluene.

The cyclopentadiene compound according to the present invention is not only useful as the charge transporting material for electrophotographic photoconductors but also suitable for use in electronic devices such as a solar battery.

Next, a description will be given of a construction of layers of the electrophotographic photoconductor in one embodiment of the present invention.

FIG. 1 shows a construction of layers of the electrophotographic photoconductor according to the present invention. In FIG. 1, the electrophotographic photoconductor comprises an electroconductive support 1 and a photoconductive layer 4 on the support 1. The electroconductive support 1 is formed as the lower layer of the photoconductor. Alternatively, a separate electroconductive material on a sheet of substrate may be formed.

The photoconductive layer 4 in FIG. 1 is constructed into a laminated structure having a charge generating layer 2 on the support 1 and a charge transporting layer 3 on the layer 2. The charge generating layer 2 is the middle layer of the photoconductor, and the charge transporting layer 3 is the upper layer thereof. The charge generating layer 2 includes a charge generating material and it may include a binder resin as required. The charge transporting layer 3 includes a charge transporting material and may include a binder resin as required.

Figure 2:
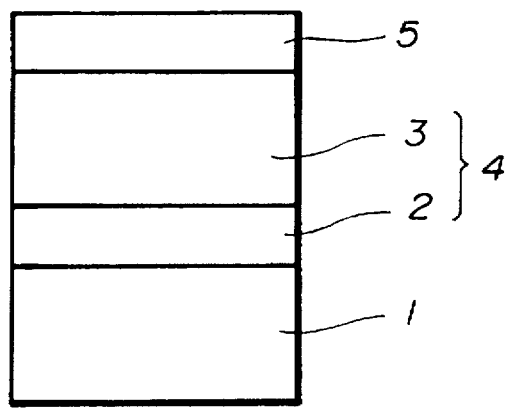
FIG. 2 is a cross-sectional view of an electrophotographic photoconductor having another construction of layers in one embodiment of the present invention.

FIG. 2 shows another construction of layers of the electrophotographic photoconductor according to the present invention. The electrophotographic photoconductor in FIG. 2 has the same construction as that in FIG. 1, except that the former includes a protective layer 5 on the photoconductive layer 4. This protective layer 5 is provided to prevent the charge transporting material in the charge transporting layer 3 from being affected by the environmental factors.

Figure 3:
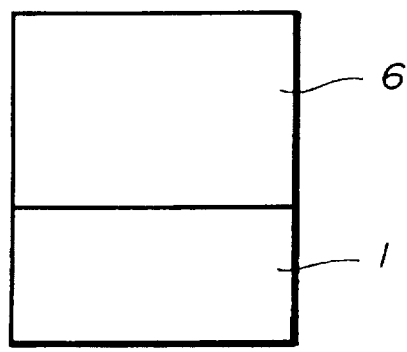
FIG. 3 is a cross-sectional view of an electrophotographic photoconductor having still another construction of layers in one embodiment of the present invention.

FIG. 3 shows still another construction of layers of the electrophotographic photoconductor according to the present invention. In FIG. 3, the electrophotographic photoconductor comprises the electroconductive support 1 and a photoconductive layer 6 on the support 1. The electroconductive support 1 is the same as that in FIG. 1. The photoconductive layer 6 is a single layer in which a charge generating material and a charge transporting material coexist. The photoconductive layer 6 may include a binder resin as required.

A protective layer on the photoconductive layer 6 may be additionally formed as the upper layer of the photoconductor in FIG. 3. Further, an intermediate layer between the support 1 and the photoconductive layer 6 may additionally be formed in the electrophotographic photoconductor in FIG. 3.

In the electrophotographic photoconductor in one embodiment of the present invention, any inorganic or organic charge generating materials which can absorb visible light and generate free charges may be used.

Examples of such charge generating materials mentioned above are: inorganic materials, such as amorphous selenium, trigonal crystsal selenium, selenium-arsenic alloy, selenium-tellurium alloy, cadmium sulfide, cadmium selenide, cadmium sulfoselenide, mercury sulfide, lead oxide, lead sulfide, and amouphous silicon; and organic materials, such as bisazo dye, polyazo dye, triarylmethane dye, thiazine dye, oxazine dye, xanthene dye, cyanine dye, styryl dye, pyrylium dye, quinacridone dye, indigo dye, perylene dye, polycyclic quinone dye, bisbenzimidazole dye, indanthrone dye, squarylium dye, anthraquinone dye, and phthalocyanine dye.

Examples of the binder resin included in the photoconductive layer in one embodiment of the present invention are: addition polymer resins of, polyaddition resins of, and polycondensation resins of polyethylene, polypropylene, acryl resin, methacryl resin, vinyl chloride resin, vinyl acetate resin, epoxy resin, polyurethane resin, phenol resin, polyester resin, alkyd resin, polycarbonate resin, silicon resin, and melamine resin. Also, the examples of the binder resin mentioned above are copolymer resins including two or more resin units mentioned above, such as vinylchloride-vinylacetate colymer resin, vinylchloride-vinylacetate-maleic anhydride copolymer resin, and poly-N-vinylcarbazole.

Examples of the electroconductive support mentioned above include a metallic sheet, drum or foil of aluminum or nickel, an aluminum-deposited plastic film, a tin-oxide-deposited plastic film, an indium-oxide-deposited plastic film, an electroconductive-material-coated paper sheet, and an electroconductive-material-coated plastic film or drum.

Next, a description will be given of a method of preparing an electrophotographic photoconductor in one embodiment of the present invention, wherein the photoconductive layer has the laminated structure as shown in FIGS. 1 and 2.

The charge generating layer 2 on the electroconductive support 1 is first formed. In order to form the charge generating layer 2, a charge generating material is deposited on the support 1 through vacuum deposition. Alternatively, the charge generating material is solved or dispersed in a suitable solvent with or without a binder resin, and it is coated to the support 1, and dried to form the charge generating layer 2 on the support 1.

When the charge generating material is dispersed in the solvent to form the charge generating layer 2, it is desirable that the average size of particles of the charge generating material dispersed therein is below 2 μm, and preferably below 1 μm. If the average particle size is too great, the smoothness of the layer surface becomes poor, and a rough surface may cause an undesired discharge phenomenon on the photoconductor. If the average particle size is too small, the cohesion of the material tends to occur, and the resistance of the layer may be increased and the number of crystal defects may be increased. The permissible lower limit of the average size of the particles of the charge generating material dispersed therein may be 0.01 μm.

Alternatively, the charge generating layer 2 on the electroconductive support 1 in one embodiment of the present invention may be formed according to the following method. A charge generating material dispersed in a solvent is ground into fine particles by using a ball mill or a homogenizer. A binder resin is added, and the binder resin and the particles of the charge generating material are mixed and well dispersed in the solvent. The solvent in which the binder resin and the particles of the charge generating material are dispersed is coated to the support 1 so that the charge generating layer 2 is formed. It is possible to uniformly disperse the biner resin and the particles of the charge generating material in the solvent by applying ultrasonic waves and dispersing them.

The ratio of the charge generating material to the binder resin in the charge generating layer in a preferred embodiment is 20–200 parts by weight of the charge generating material to 100 parts by weight of the binder resin.

The charge generating layer 2 formed according to the above-described method should be 0.01–10 μm thick, preferably 0.1–5 μm thick.

The charge transporting layer 3 on the charge generating layer 2 is secondly formed. In order to form the charge transporting layer 3, a charge transporting material is solved or dispersed in a suitable solvent with or without a binder resin, and it is coated to the charge generating layer 2 and dried.

Examples of the solvent used to form the charge transporting layer 3 are N,N-dimethylformamido, toluene, xylene, monochlorbenzene, 1,2-dichlorethane, dichlormethane, 1,1,1-trichlorethane, 1,1,2-trichlorethylene, tetrahydrofuran, methyl ethyl ketone, cyclohexane, ethyl acetate, and butyl acetate.

The ratio of the charge transporting material to the binder resin in the charge transporting layer 3 in a preferred embodiment is 20-200 parts by weight of the charge transporting material to 100 parts by weight of the binder resin.

The charge transporting layer 3 formed according to the above-described method should be 5-50 μm thick, and preferably 5-30 μm thick.

Next, a description will be given of a method of producing an electrophotographic photoconductor in one embodiment of the present invention, wherein the photoconductive layer is the single layer as shown in FIG. 3.

In order to form the photoconductive layer 6 on the electroconductive support 1, the charge generating material and the charge transporting material are solved or dispersed in a suitable solvent with the binder resin, and the solvent is coated to the support 1 and dried.

The ratio of the charge generating material to the binder resin in the photoconductive layer 6 in a preferred embodiment is 20-200 parts by weight of the charge generating material to 100 parts by weight of the binder resin. The ratio of the charge transporting material to the binder resin in the photoconductive layer 6 in a preferred embodiment is 20-200 parts by weight of the charge transporting material to 100 parts by weight of the binder resin.

The photoconductive layer 6 formed according to the above-described method should be 7-50 μm thick, and preferably 10-30 μm thick.

The intermediate layer between the support 1 and the photoconductive layer 6 described above is provided for the purpose of adhesion or barrier. Examples of the source material of the above intermediate layer are: the above-mentioned examples of the binder resin, polyvinyl alcohol, ethyl cellulose, carboxymethyl cellulose, vinylchloride-vinylacetate copolymer, vinylchloride-vinylacetate-maleic anhydride copolymer, casein, N-alkoxymethylnylon, with or without tin oxide or indium dispersed, and a deposition film such as aluminum oxide, zinc oxide, and silicon oxide. The intermediate layer in a preferred embodiment should be less than 1 μm thick.

Examples of the source material of the above protective layer are: the above-mentioned resins with or without tine oxide or indium dispersed, and any of organic plasma polymerization films. The organic plasma polymerization films may include any of oxygen, nitrogen, halogens, group III atoms, and group V atoms in the periodic table.

[EXAMPLES]

Next, a description will be given of examples of the cyclopentadiene compounds according to the present invention and examples of the electrophotographic photoconductors comprising one cyclopentadiene compound. Hereinafter, the examples of the cyclopentadiene compounds are referred to as the compound examples, and the examples of the electrophographic photoconductors are referred to as the medium examples.

Compound Example 42

In order to prepare a compound example of the cyclopentadiene compound (Compound No.42), 3.3 g (0.01 mol) of dimethyl-4,4'-benzyldicarboxylate, and 2.1 g (0.01 mol) of dibenzylketone are solved in 150 ml of ethyl alcohol. 3.2 g (0.02 mol) of potassium carbonate is added. This solution is subjected to reflux for 2 hours while it is stirred, to cause the reaction to occur. After it is cooled to normal temperature, it is transferred to a water bath. A compound is extracted from the solution by using chloroform. The extracted compound in the chloroform is dired with anhydrous magnesium sulfate, and the chloroform is eliminated. The remaining compound is processed through silica gel chromatography by using a 1,2-dichloroethane solvent, to produce a crude object material. The crude object material is crystalized by using ethyl alcohol so that 1.0 g of a genuine object material of the cyclopentadiene compound is obtained.

The melting point of this compound (the Compound Example 42) is 176.0°-176.1° C. The result of the elemental analysis is: carbon C 79.35 (79.19); and hydrogen H 5.12 (4.83). The value in parentheses indicates the theoretical value.

Figure 4:
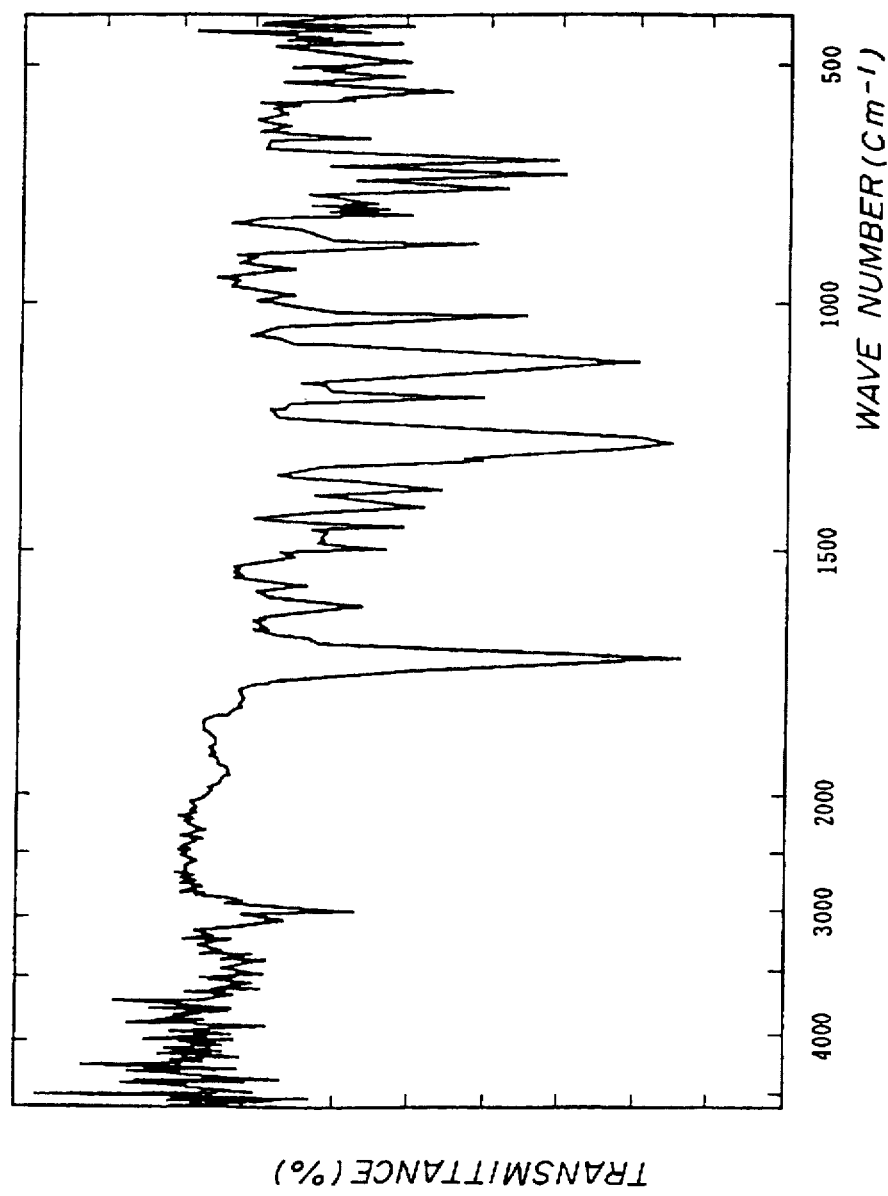
FIG. 4 is a graph showing an infrared absorption spectrum of a cyclopentadiene derivative compound in one embodiment of the present invention.

FIG. 4 shows an infrared absorption spectrum of this cyclopentadiene compound.

Compound Example 43

In order to prepare a compound example of the cyclopentadiene compound (Compound No.43), 2.5 g (0.005 mol) of the Compound Example 42 mentioned above (Compound No.42) and 1.4 g (0.01 mol) of butyl cyanoacetate are solved in dichloromethane. This solution is cooled by using ice, and 1.9 g (0.01 mol) of titanium tetrachloride is dropped while the solution is stirred. Then, 4.1 g (0.04 mol) of N-methylmorpholine is dropped, and the solution is stirred at normal temperature for five hours. This solution is transferred to a water bath. A compound is extracted from the solution by using chloroform. The extracted compound in the chloroform is dried with anhydrous magnesium sulfate, and the chloroform is eliminated. The remaining compound is processed through silica gel chlomatography by using a 1,2-dichloroethane solvent, to produce a crude object material. The crude object material is crystalized by using ethyl alcohol so that 2.4 g of a genuine object material of the cyclopentadiene compound is obtained.

The melting point of this compound is 157.5°-159.0° C. The result of the elemental analysis is: carbon C 76.89 (77.03); hydrogen H 5.28 (5.33); and nitrogen N 2.32 (2.25). The value in parentheses indicates the theoretical value.

Figure 5:
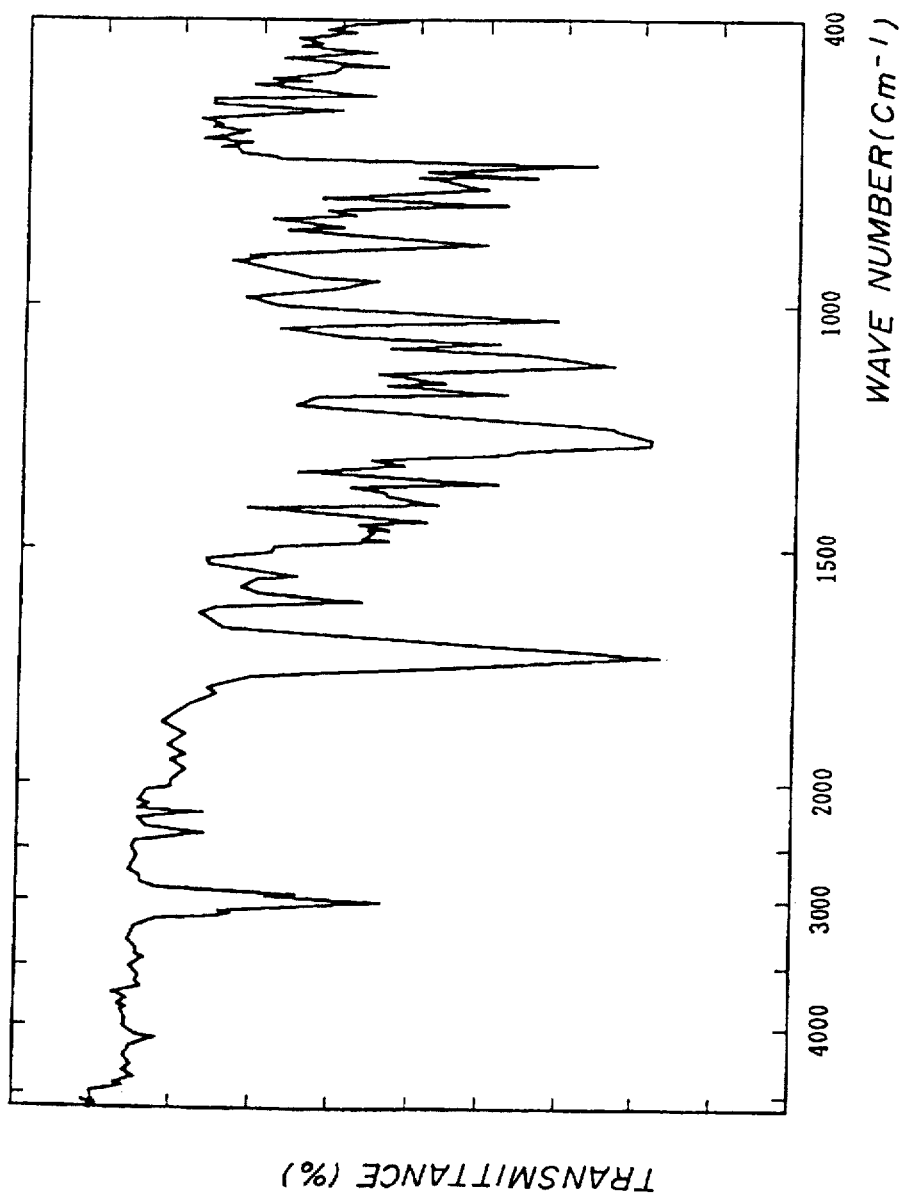
FIG. 5 is a graph showing an infrared absorption spectrum of another cyclopentadiene derivative compound in one embodiment of the present invention.

FIG. 5 shows an infrared absorption spectrum of this cyclopentadiene compound.

Example 1

In order to prepare a Medium Example 1 of the electrophotographic photoconductor, 5 parts by weight of a bisazo dye, 2.5 parts by weight of butyral resin (Denka Butyral Resin #3000-2 from Denki Kagaku Kogyo Co., Ltd.), and 92.5 parts by weight of tetrahydrofuran are dispersed by using a ball mill for 12 hours. The bisazo dye mentioned above consists of a composition represented by formula (IV):

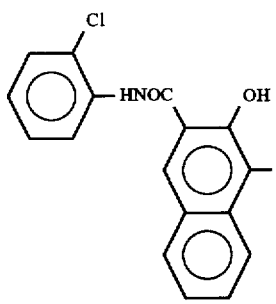 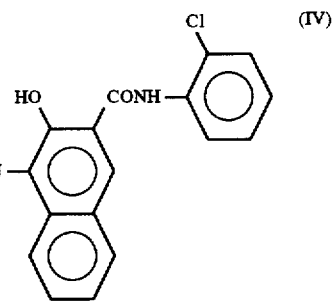

(IV)

A certain amount of tetrahydrofuran is added so that 2 wt % of the dispersed solution is obtained. This solution is applied to a 100-μm thick, aluminum-deposited polyester film by following formula (V) is used instead of the bisazo dye represented by the above formula (IV).

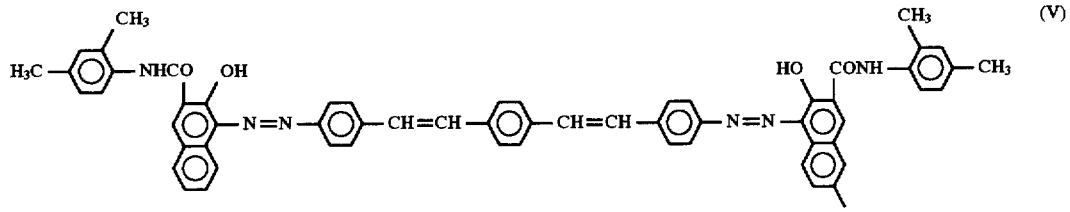

(V)

using a doctor blade. After dried, a 1.0-μm thick charge generating layer on the support is formed.

In order to form a charge transporting layer on the above-mentioned charge generating layer, 6 parts by weight of the compound example 1 (Compound No.1), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is applied to the charge generating layer by using a doctor blade. After dried, a 20.0-μm thick charge transporting layer on the charge generating layer is formed. This Example 1 (Medium No.1, Compound No.1) of the electrophotographic photoconductor is formed, which has a laminated structure including the aluminum electrode, the charge generating layer, and the charge transporting layer.

Examples 2–7

Examples 2, 3, 4, 5, 6 and 7 (Medium Nos.2, 3, 4, 5, 6 and 7) of the electrophotographic photoconductors are prepared in the same manner as the above Example 1 except that Compound Examples 2, 19, 26, 27, 42 and 43 (Compound Nos.2, 19, 26, 27, 42 and 43) are respectively used instead of the above Compound Example 1.

Comparative Example 1 (C/E NO.1)

A comparative example 1 (Medium No.8) is prepared in the same manner as the above Example 1 except that 2,4,7-trinitrofluorenone (TNF) is used instead of the above Compound Example 1.

Example 8

In order to prepare a medium example (Medium No.9) of the electrophotographic photoconductor, the charge generating layer on the photoconductive support is formed in the same manner as that of the above Example 1 except that a bisazo dye consisting of a composition represented by the In order to form the charge transporting layer on the above charge generating layer, 6 parts by weight of the Compound Example 1 (Compound No.1), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is applied to the above charge generating layer by using a doctor blade. After dried, a 20.0-μm thick charge transporting layer on the charge generating layer is formed. The Example 8 (Medium No.9, Compound No.1) is thus formed, which has a laminated structure including the aluminum electrode, the charge generating layer, and the charge transporting layer.

Examples 9–17

Examples 9, 10, 11, 12, 13, 14, 15, 16 and 17 (Medium Nos.10, 11, 12, 13, 14, 15, 16, 17 and 18) are prepared in the same manner as the above Example 8 except that Compound Examples 2, 19, 26, 27, 42, 43, 44, 63 and 113 (Compound Nos.2, 19, 26, 27, 42, 43, 44, 63 and 113) are respectively used instead of the above Compound Example 1.

Comparative Example 2 (C/E NO.2)

A comparative example 2 (Medium No.20) is prepared in the same manner as the above Example 8 except that 2,4,7-trinitrofluorenone (TNF) is used instead of the above Compound Example 1.

Example 18

In order to prepare a medium example (Medium No.21) of the photoconductor, the charge generating layer on the electroconductive support is formed in the same manner as that of the above Example 1 except that a trisazo dye consisting of a composition represented by the following formula (VI) is used instead of the bisazo dye represented by the above formula (IV).

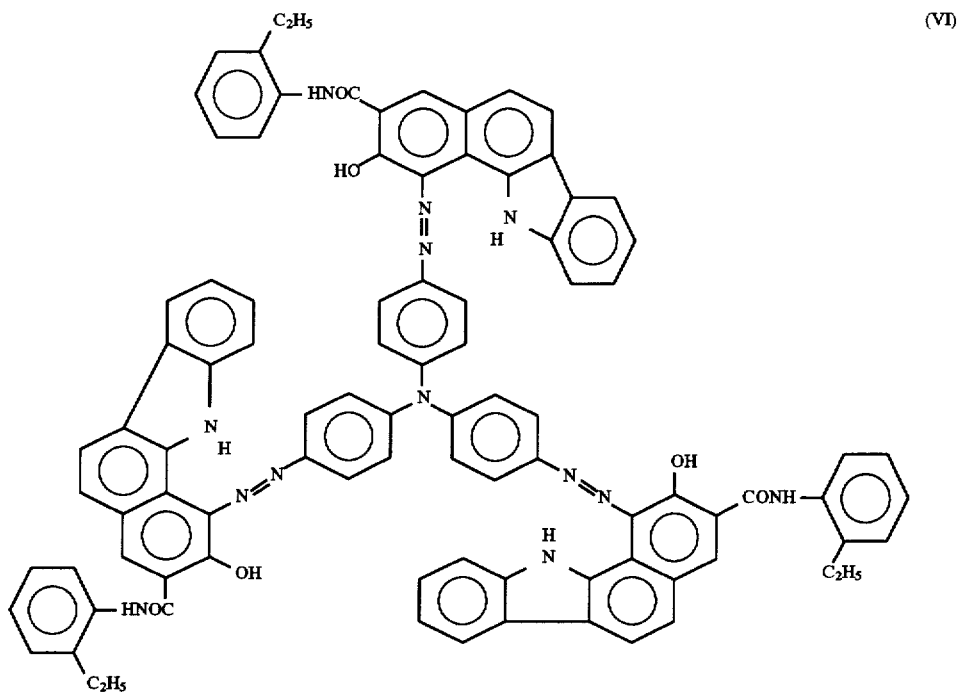

(VI)

In order to form the charge transporting layer on the above charge generating layer, 6 parts by weight of the Compound Example 2 (Compound No.2), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is applied to the above charge generating layer by using a doctor blade. After dried, a 20.0-μm thick charge transporting layer on the charge generating layer is formed. The Example 18 (Medium No.21, Compound No.2) is thus formed, which has a laminated structure including the aluminum electrode, the charge generating layer, and the charge transporting layer.

Examples 19–20

Examples 19 and 20 (Medium Nos.22 and 23) are prepared in the same manner as the above Example 18 except that Compound Examples 26 and 42 (Compound Nos.26 and 42) are respectively used instead of the above Compound Example 2.

Comparative Example 3 (C/E NO.3)

A comparative example 3 (Medium No.24) is prepared in the same manner as the above Example 18 except that 2,4,7-trinitrofluorenone (TNF) is used instead of the above Compound Example 2.

Example 21

In order to prepare a medium example (Medium No.25) of the electrophotographic photoconductor, 5 parts by weight of an X-type, non-metallic phthalocyanine (Fastogen Blue 812BS from DIC Co., Ltd.), 5 parts by weight of polyvinyl butyral resin (S-Lec BLS from Seisui Kagaku Co., Ltd.), and 90 parts by weight of tetrahydrofuran are dispersed by using a ball mill for 12 hours. A certain amount of tetrahydrofuran is added so that 2 wt % of the dispersed solution is obtained. This solution is applied to a 100-μm thick, aluminum-deposited polyester film by using a doctor blade. After dried, a 0.5-μm thick charge generating layer on the support is formed.

In order to form a charge transporting layer on the above charge generating layer, 6 parts by weight of the Compound Example 1 (Compound No.1), 10 parts by weight of polycarbonate resin (K-1300 from Teijin Kasei Co., Ltd.), and 94 parts by weight of tetrahydrofuran are solved or dispersed. This solution is applied to the charge generating layer by using a doctor blade. After dried, a 20.0-μm thick charge transporting layer on the charge generating layer is formed. The Example 1 (Medium No.25, Compound No.1) is thus formed, which has a laminated structure including the aluminum electrode, the charge generating layer, and the charge transporting layer.

Examples 22–30

Examples 22, 23, 24, 25, 26, 27, 28, 29 and 30 (Medium Nos.26, 27, 28, 29, 30, 31, 32, 33 and 34) are prepared in the same manner as the above Example 21 except that Compound Examples 2, 19, 26, 27, 42, 43, 44, 63 and 113 (Compound Nos.2, 19, 26, 27, 42, 43, 44, 63 and 113) are respectively used instead of the above Compound Example 1.

Example 31

In order to prepare a medium example (Medium No.35) of the electrophotographic photoconductor, 0.5 g of the bisazo dye represented by the above formula (IV), 10 g of 10-wt % tetrahydrofuran solution of polycarbonate Z (Teijin Kasei Co., Ltd.), and 9 g of tetrahydrofuran are dispersed by using a ball mill. The 10-wt % polycarbonate Z solution, the Compound Example 2, and a positive-hole transporting material, consisting of a composition represented by the following formula (VII), are added so that 2 wt % of the dye, 50 wt % of the polycarbonate Z, 20 wt % of the cyclopentadiene compound, and 28 wt % of the positive-hole transporting material are obtained. This solution is well stirred and coated to a 75-μm thick, aluminium-deposited (1000 Å) polyester film by using a doctor blade. After dried, a 15-μm thick photoconductive layer on the support is formed. The Example 31 (Medium No.35, Compound No.2) is thus formed, wherein the photoconductive layer is a single layer.

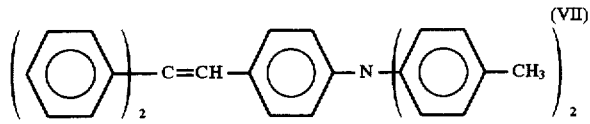

Examples 32–36

Examples 32, 33, 34, 35 and 36 (Medium Nos.36, 37, 38, 39 and 40) are prepared in the same manner as the above Example 31 except that Compound Examples 19, 26, 27, 42 and 43 (Compound Nos.19, 26, 27, 42 and 43) are respectively used instead of the above Compound Example 2.

Comparative Example 4 (C/E NO.4)

A comparative example 4 (Medium No.41) is prepared in the same manner as the above Example 32 except that no cyclopentadiene compound is used.

Example 37

In order to prepare a medium example (Medium No.42) of the electrophotographic photoconductor, 0.5 g of X-type, non-metallic phthalocyanine, 10 g of 10-wt % tetrahydrofuran solution of Polycarbonate Z (Teijin Kasei Co., Ltd.), and 9 g of tetrahydrofuran are dispersed by using a ball mill. The 10-wt % polycarbonate Z solution, the Compound Example 2, and the positive-hole transporting material, consisting of the composition represented by the above formula (VII), are added, so that 2 wt % of the dye, 50 wt % of the polycarbonate Z, 20 wt % of the cyclopentadiene compound, and 28 wt % of the positive-hole transporting material are obtained. This solution is well stirred and applied to a 75-μm thick, aluminium-deposited (1000 Å) polyester film by using a doctor blade. After dried, a 15-μm thick photoconductive layer on the support is formed. The Example 37 (Medium No.42, Compound No.2) is thus formed, wherein the photoconductive layer is a single layer.

Examples 38–42

Examples 38, 39, 40, 41 and 42 (Medium Nos.43, 44, 45, 46 and 47) are prepared in the same manner as the above Example 37 except that Compound Examples 19, 26, 27, 42 and 43 (Compound Nos.19, 26, 27, 42 and 43) are respectively used instead of the above Compound Example 2.

Comparative Example 5 (C/E NO.5)

A comparative example 5 (Medium No.48) is prepared in the same manner as the above Example 38 except that no cyclopentadiene compound is used.

An evaluation test is conducted by using an electrostatic copy analyzer ("SP-428" from Kawaguchi Works Co., Ltd.) to evaluate photosensitive characteristics of the above examples of the electrophotographic photoconductors which are prepared in the manner described above. The evaluation test is performed as follows.

The above examples of the electrophotographic photoconductors are subjected to +6 KV corona charge so that the surfaces of the photoconductors are positively charged. The examples rest on a dark place for 20 seconds. The surface potential Vo (volt) of each example after the resting is measured. After the measurement, light from a tungsten lamp is irradiated to the surface of the example to make the illuminance thereof to be 20 lux, and the quantity $E_{1/2}$ (lux-sec) of the light exposure, needed to change the surface potential of the example from the initial potential Vo to half (Vo/2) of the initial potential, is measured. The results of the above evaluation test for the respective examples are listed in TABLES 21 through 23 which follows.

TABLE 21

| EXAMPLE NO. | MEDIUM NO. | COMPOUND NO. | $V_O$ (V) | $E_{1/2}$ (1 ux · sec) |
|---|---|---|---|---|
| 1 | 1 | 1 | 1650 | 40.1 |
| 2 | 2 | 2 | 1940 | 27.6 |
| 3 | 3 | 19 | 2180 | 40.6 |
| 4 | 4 | 26 | 2000 | 28.9 |
| 5 | 5 | 27 | 1960 | 30.1 |
| 6 | 6 | 42 | 1950 | 28.9 |
| 7 | 7 | 43 | 1800 | 23.1 |
| C/E NO.1 | 8 | TNF | 1700 | 72.3 |
| 8 | 9 | 1 | 1800 | 18.1 |
| 9 | 10 | 2 | 1880 | 10.4 |
| 10 | 11 | 19 | 2120 | 12.3 |
| 11 | 12 | 26 | 2110 | 13.4 |
| 12 | 13 | 27 | 1920 | 17.4 |
| 13 | 14 | 42 | 1520 | 4.4 |
| 14 | 15 | 43 | 1500 | 3.8 |
| 15 | 16 | 44 | 1490 | 3.3 |
| 16 | 17 | 63 | 1800 | 17.6 |
| 17 | 18 | 113 | 1890 | 17.9 |
| C/E NO.2 | 20 | TNF | 1550 | 51.9 |

TABLE 22

| EXAMPLE NO. | MEDIUM NO. | COMPOUND NO. | $V_O$ (V) | $E_{1/2}$ (1 ux · sec) |
|---|---|---|---|---|
| 18 | 21 | 2 | 1760 | 10.2 |
| 19 | 22 | 26 | 1820 | 23.5 |
| 20 | 23 | 42 | 1530 | 24.9 |
| C/E NO.3 | 24 | TNF | 1500 | 50.1 |
| 21 | 25 | 1 | 1970 | 14.3 |
| 22 | 26 | 2 | 1940 | 6.8 |
| 23 | 27 | 19 | 1980 | 7.1 |
| 24 | 28 | 26 | 1950 | 9.2 |
| 25 | 29 | 27 | 1800 | 13.8 |
| 26 | 30 | 42 | 1700 | 1.6 |
| 27 | 31 | 43 | 1630 | 1.3 |
| 28 | 32 | 44 | 1600 | 0.9 |
| 29 | 33 | 63 | 1630 | 14.1 |
| 30 | 34 | 113 | 1680 | 14.5 |
| 31 | 35 | 2 | 1390 | 1.14 |
| 32 | 36 | 19 | 1550 | 1.22 |
| 33 | 37 | 26 | 1440 | 1.23 |
| 34 | 38 | 27 | 1530 | 1.34 |
| 35 | 39 | 42 | 1550 | 1.22 |
| 36 | 40 | 43 | 1500 | 1.09 |

TABLE 23

| EXAMPLE NO. | MEDIUM NO. | COMPOUND NO. | $V_O$ (V) | $E_{1/2}$ (1 ux · sec) |
|---|---|---|---|---|
| C/E NO.4 | 41 | NONE | 1500 | 1.68 |
| 37 | 42 | 2 | 1300 | 0.79 |
| 38 | 43 | 19 | 1500 | 0.93 |
| 39 | 44 | 26 | 1440 | 0.75 |
| 40 | 45 | 27 | 1580 | 0.75 |
| 41 | 46 | 42 | 1510 | 0.74 |
| 42 | 47 | 43 | 1490 | 0.68 |
| C/E NO.5 | 48 | NONE | 1530 | 1.23 |

As described in the foregoing, the cyclopentadiene derivative compounds of the present invention can be produced through a simple, efficient production method. The cyclopentadiene compounds of the present invention are readily solved in a binder resin. The cyclopentadiene derivative compounds of the present invention have excellent charge acceptance and charge transport abilities, and provide an excellent charge transporting function by including the same in the photoconductive layer. The above evaluation test has verified that the electrophotographic photoconductor comprising one cyclopentadiene derivative compound of the present invention provides a good light sensitivity and high durability.

Next, a description will be given of an electrophotographic photoconductor comprising one cyclopentadiene compound in another embodiment of the present invention. The acceptor compound in this embodiment is a 2,3-diphenylindene compound which is also one of the cyclopentadiene derivative compounds of the present invention, and this compound consists of a composition represented by formula (VIII):

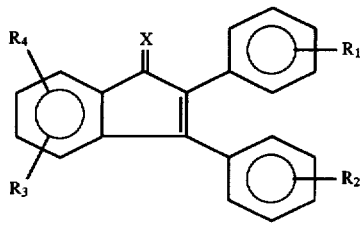

(VIII)

wherein $R_1$, $R_2$, $R_3$ and $R_4$ independently represent a hydrogen atom, a halogen atom, a cyano group, a nitro group, or an alkyl group which may have a substituent, wherein X represents:
  an oxygen atom =O;
  a substitution group of a formula =C—[A][B] wherein A and B independently represent a hydrogen atom, a halogen atom, a cyano group, an aromatic group which may have a substituent, or a group —COOR$_6$ wherein R$_6$ represents an alkyl group which may have a substituent, or an aromatic group which may have a substituent; or
  a substitution group of a formula =N—R$_5$ where R$_5$ represents a cyano group, an alkyl group which may have a substituent, or an aromatic group which may have a substituent.

Specific examples of the substituents related to the above formula (VIII) will be given here.

The alkyl group for each of $R_1$ through $R_4$ in the above formula (VIII) is one from among groups including methyl, ethyl, isopropyl, t-butyl, n-butyl, hexyl, octyl, one of cycloalkyl groups, such as cyclohexyl and cyclopentyl, one of halogen alkyl groups, such as trifluoromethyl, chloromethyl, bromoethyl and fluoropropyl, and a benzyl group.

The halogen atom for each of $R_1$ through $R_4$ in the above formula (VIII) is one from among atoms including fluorine, chlorine, bromine, and iodine.

Examples of the aromatic group for each of A and B in the formula =C—[A][B] are phenyl, naphthyl, anthracene, and pyrene. A substituent of a hydrogen atom in the aromatic group mentioned above is one from among various groups including chloro, bromo, methyl, ethyl, isopropyl, t-butyl, n-butyl, nitro, cyano, methoxyl, ethoxyl, acetoxyl, methoxycarbonyl, ethoxycarbonyl, buthoxycarbonyl, methylcarbonyl, ethylcarbonyl, N,N-dimethylamino, benzoxyamino, N,N-dimethylamido, methylthioxy, trifluoromethyl, and phenyl.

Examples of the alkyl group for each of $R_5$ and $R_6$ are the same as those for each of $R_1$ through $R_4$ in the above formula (VIII).

Examples of the aromatic group for each of $R_5$ and $R_6$ are the same as those for each of A and B in the formula =C—[A][B] mentioned above.

By taking into account the relationship between the above formula [I] and the above formula (VIII), it is readily understood that $R_3$ and $R_4$ in the formula [I], related to the previously-described cyclopentadiene compound of the present invention, may represent a phenyl group which may have a substituent, the phenyl group being formed integrally with the cyclopentadiene compound.

Examples of the 2,3-diphenylindene compounds according to the present invention, each consisting of a composition represented by the above formula (VIII), are listed in TABLES 31 through 34 which follows. However, the present invention is not limited to these examples only.

TABLE 31

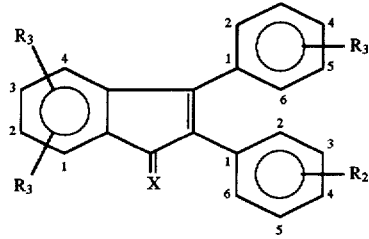

| COMPOUND NO. | X | $R_1$ | $R_2$ | $R_2$ | $R_4$ |
|---|---|---|---|---|---|
| 1 | =O | H | H | H | H |
| 2 | =C(CN)(CN) | H | H | H | H |
| 3 | =C(CN)(COOCH$_3$) | H | H | H | H |
| 4 | =C(CN)(COOC$_2$H$_5$) | H | H | H | H |
| 5 | =C(CN)(COOC$_3$H$_7$) | H | H | H | H |
| 6 | =C(CN)(COOC$_4$H$_9$) | H | H | H | H |
| 7 | =C(CN)(COOC$_6$H$_{13}$) | H | H | H | H |
| 8 | =C(CN)(COOC$_8$H$_{17}$) | H | H | H | H |

TABLE 31-continued

[Structure: indanone-type with R₃ positions on left benzene ring (1,2,3,4), X at carbonyl position, and two phenyl rings with R₃ (3,4,5) and R₂ (2,3,4,5,6) substituents]

| COMPOUND NO. | X | R₁ | R₂ | R₃ | R₄ |
|---|---|---|---|---|---|
| 9 | =C(COOCH₃)₂ | H | H | H | H |
| 10 | =C(COOC₂H₅)₂ | H | H | H | H |
| 11 | =C(COOC₄H₉)₂ | H | H | H | H |

TABLE 32

| COMPOUND NO. | X | R₁ | R₂ | R₃ | R₄ |
|---|---|---|---|---|---|
| 12 | =C(CN)(4-CH₃-C₆H₄) | H | H | H | H |
| 13 | =C(CN)(3-CH₃-C₆H₄) | H | H | H | H |
| 14 | =C(CN)(2-CH₃-C₆H₄) | H | H | H | H |
| 15 | =C(CN)(2-Cl-C₆H₄) | H | H | H | H |
| 16 | =C(CN)(4-Cl-C₆H₄) | H | H | H | H |

TABLE 32-continued

| COMPOUND NO. | X | R₁ | R₂ | R₃ | R₄ |
|---|---|---|---|---|---|
| 17 | =C(CN)(4-OCH₃-C₆H₄) | H | H | H | H |
| 18 | =C(CN)(3-OCH₃-C₆H₄) | H | H | H | H |
| 19 | =C(CN)(2,4-Cl₂-C₆H₃) | H | H | H | H |
| 20 | =N—CN | H | H | H | H |
| 21 | =N(2-CH₃-C₆H₄) | H | H | H | H |
| 22 | =N(2-HC(CH₃)₂-C₆H₄) | H | H | H | H |

TABLE 33

| COMPOUND NO. | X | R₁ | R₂ | R₃ | R₄ |
|---|---|---|---|---|---|
| 23 | =N(2-CF₃-C₆H₄) | H | H | H | H |
| 24 | =N(2,6-(CH₃)₂-C₆H₃) | H | H | H | H |
| 25 | =N(2,6-(C₂H₅)₂-C₆H₃) | H | H | H | H |
| 26 | =N—C₄H₉ | H | H | H | H |
| 27 | =O | 4-CH₃ | H | 2-CH₃ | H |

TABLE 33-continued

| COMPOUND NO. | X | R₁ | R₂ | R₃ | R₄ |
|---|---|---|---|---|---|
| 28 | =C(CN)(CN) | 4-CH₃ | H | 2-CH₃ | H |
| 29 | =C(CN)(COOC₄H₉) | 4-CH₃ | H | 2-CH₃ | H |
| 30 | =O | 4-CH₃ | 4-CH₃ | 2-CH₃ | H |
| 31 | =C(CN)(CN) | 4-CH₃ | 4-CH₃ | 2-CH₃ | H |
| 32 | =C(CN)(COOC₄H₉) | 4-CH₃ | H | 2-CH₃ | H |
| 33 | =C(CN)(CN) | 4-CH₃ | H | 2-CH₃ | H |

TABLE 34

| COMPOUND NO. | X | R₁ | R₂ | R₃ | R₄ |
|---|---|---|---|---|---|
| 34 | =C(CN)(COOC₂H₅) | 3-CH₃ | H | 3-C₄H₉ | H |
| 35 | =C(COOC₄H₉)(COOC₄H₉) | 4-CF₃ | H | H | H |
| 36 | =N-(2-CH₃-C₆H₄) | 4-Br | H | 3-Br | 4-Br |
| 37 | =C(CN)(2-CH₃-C₆H₄) | 4-NO₂ | H | H | H |
| 38 | =C(CN)(COOC₄H₉) | 4-CN | H | H | H |
| 39 | =O | H | H | 2-NO₂ | H |
| 40 | =C(CN)(COOC₄H₉) | 4-Br | H | 2-Br | H |

TABLE 34-continued

| COMPOUND NO. | X | R₁ | R₂ | R₃ | R₄ |
|---|---|---|---|---|---|
| 41 | =C(CN)(COOC₂H₅) | 4-Cl | H | H | H |
| 42 | =C(CN)(COOC₄H₉) | H | H | 2-Br | H |

The 2,3-diphenylindene compound, consisting of the composition represented by the above formula (VIII), is prepared through the following production methods.

The 2,3-diphenylindene compound in one embodiment of the present invention can be prepared by making a 2,3-diphenyl-indenone compound react with a methylene compound in the presence of an acid catalyst or basic catalyst. The reaction formula is as follows.

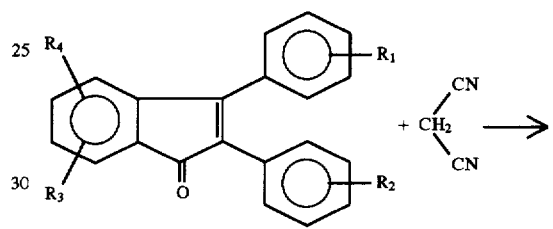

(VIII')

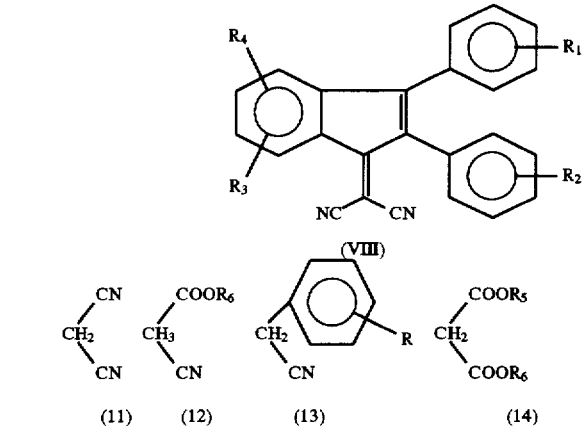

(VIII)

$$\underset{(11)}{\overset{CN}{\underset{CN}{\diagdown}}CH_2\diagup} \quad \underset{(12)}{\overset{COOR_6}{\underset{CN}{\diagdown}}CH_3\diagup} \quad \underset{(13)}{\overset{CN}{\underset{CN}{\diagdown}}CH_2\diagup}R \quad \underset{(14)}{\overset{COOR_5}{\underset{COOR_6}{\diagdown}}CH_2\diagup}$$

where $R_1$ through $R_6$ in this reaction formula are the same as those described above, and R in this reaction formula is the same as the aromatic group for each of A and B in the formula =C—[A][B] mentioned above.

The 2,3-diphenyl-indenone compound mentioned above consists of a composition represented by the above formula (VIII'). The methylene compound mentioned above consists of a composition represented by one of the above formulas (11) through (14). The above reaction is in accordance with the known Lewis acid-base concept.

Examples of the acid catalyst mentioned above are: titanium tetrachloride, zinc chloride, aluminium chloride, and boron trifluoride. Also, examples of the basic catalyst mentioned above are: organic bases, such as N-methylmorpholine, N-methylpiperidine, pyridine, piperidine, and triethylamin; and inorganic bases, such as sodium acetate, potassium acetate, ammonium acetate, sodium carbonate, and potassium carbonate.

The reaction to prepare the 2,3-diphenylindene compound mentioned above is performed with or without a solvent at temperatures from −20° C. to 150° C., and preferably temperatures from 0° C. to 100° C. Examples of the solvent mentioned above are dichloromethane, dichloroethane, tetrahydrofuran, dioxane, benzene, and toluene.

In addition, the 2,3-diphenylindene compound consisting of the composition represented by the above formula (VIII) can be prepared by making the 2,3-diphenyl-indenone compound (VIII') react with an aniline compound ($H_2N$—$R_5$) in the presence of an acid catalyst. The reaction formula is as follows.

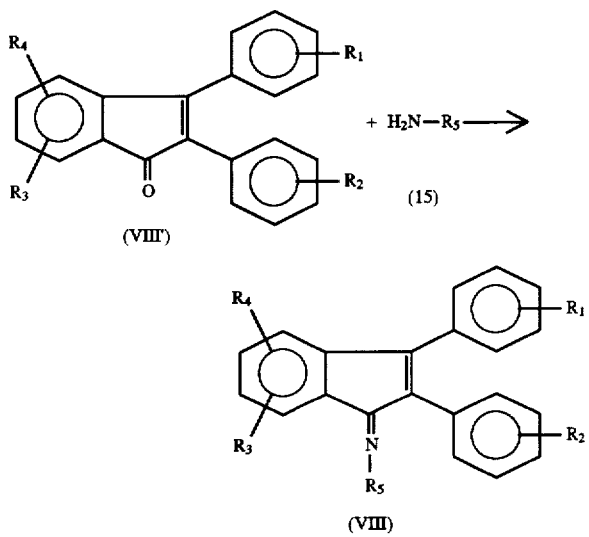

The aniline compound mentioned above consists of a composition represented by the formula (15): $H_2N$—$R_5$. The above reaction is also in accordance with the known Lewis acid-base concept.

Examples of the acid catalyst mentioned above are: titanium tetrachloride, zinc chloride, aluminium chloride, and boron trifluoride.

The reaction to prepare the 2,3-diphenylindene compound mentioned above is performed with or without a solvent at temperatures from −20° C. to 150° C., and preferably temperatures from 0° C. to 100° C. Examples of the solvent mentioned above are dichloromethane, dichloroethane, tetrahydrofuran, idoxane, benzene, and toluene.

Further, the 2,3-diphenylindene compound consisting of the composition represented by the above formula (VIII) can be prepared by making the 2,3-diphenyl-indenone compound (VIII') react with a diimido compound (which consists of a composition represented by the formula $(CH_3)_3$Si—N=C=N—Si$(CH_3)_3$) in the presence of an acid catalyst.

Examples of the acid catalyst mentioned above are: titanium tetrachloride, zinc chloride, aluminium chloride, and boron trifluoride.

The reaction to prepare the 2,3-diphenylindene compound mentioned above is performed with or without a solvent at temperatures from 0° C. to 150° C., and preferably temperatures from 0° C. to 100° C. Examples of the solvent mentioned above are dichloromethane, dichloroethane, tetrahydrofuran, dioxane, benzene, and toluene.

The 2,3-diphenylindene compound in one embodiment of the present invention is not only useful as the charge transporting material for the electrophotographic photoconductors but also suitable for use in electronic devices such as a solar battery.

[EXAMPLES]

Next, a description will be given of examples of 2,3-diphenylindene compounds according to the present invention and examples of electrophotographic photoconductors comprising one 2,3-diphenylindene compound according to the present invention. Hereinafter, the examples of the 2,3-diphenylindene compounds are referred to as the compound examples, and the examples of the electrophotographic photoconductors are referred to as the medium examples.

Compound Example 2

In order to prepare a compound example of the 2,3-diphenylindene compound (Compound No.2), 5.7 g (0.02 mol) of 2,3-diphenyl-1-indenone and 2.6 g (0.04 mol) of malononitrile are solved in 100 ml of pyridine. This solution is subjected to reflux in the presence of nitrogen gas for 4 hours to cause the reaction to occur. After it is cooled to normal temperature, it is transferred to a water bath. Hydrochloric acid is added to make the solution acidic, and a compound is extracted from the solution by using toluene. The extracted compound in the toluene is dried with anhydrous magnesium sulfate, and the toluene is eliminated. The remaining compound is processed through silica gel chlomatography by using a toluene solvent, to produce a crude object material. The crude object material is subjected to crystalization from ethyl alcohol so that 4.9 g of genuine object material is obtained.

The melting point of this compound (the Compound No.2) is 180.5°–182.1° C. The result of the elemental analysis is: carbon C 87.28 (87.25); hydrogen H 4.04 (4.27); and nitrogen N 8.45 (8.48). The value in parentheses indicates the theoretical value.

Figure 6:
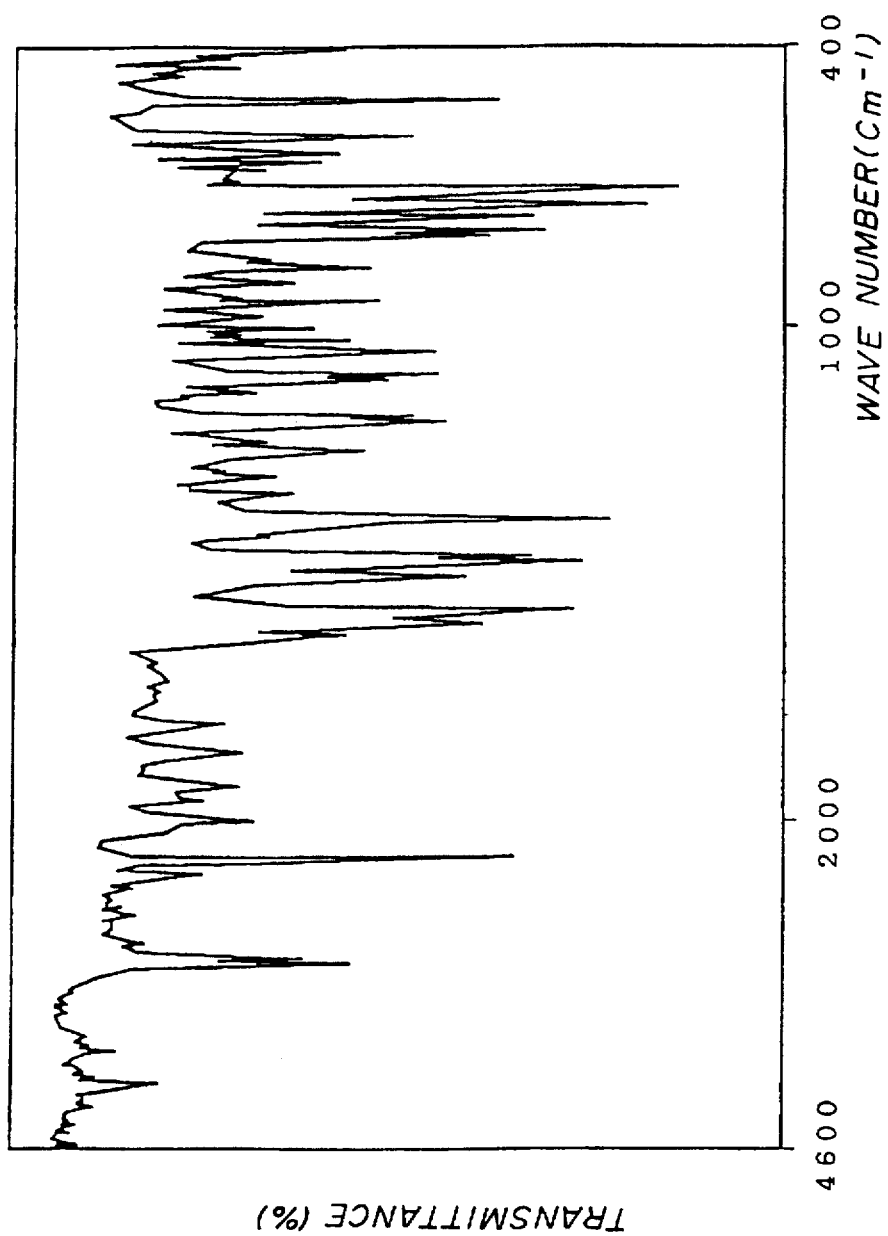
FIG. 6 is a graph showing an infrared absorption spectrum of a 2,3-diphenylindene compound in one embodiment of the present invention.

FIG. 6 shows an infrared absorption spectrum of this 2,3-diphenylindene compound.

Compound Example 6

In order to prepare a compound example of the 2,3-diphenylindene compound (Compound No.6), 5.7 g (0.02 mol) of 2,3-diphenyl-1-indenone and 5.6 g (0.04 mol) of cyanoacetic acid-n-butyl alcohol ester are solved in dichloromethane. This solution is cooled by ice while it is stirring. 7.6 g (0.04 mol) of titanium tetrachloride is dropped to this solution, and 8.2 g (0.08 mol) of N-methylmorpholine is dropped. The solution is stirred at normal temperature for 5 hours. After the stirring, the solution is transferred to a water bath. A compound is extracted from the solution by using chloroform. The extracted compound in the chloroform is dried with anhydrous magnesium sulfate, and the toluene is eliminated. The remaining compound is processed through silica gel chlomatography by using a toluene solvent, to produce a crude object material. The crude object material is crystalized by using ethyl alcohol so that 5.4 g of genuine object material is obtained.

The melting point of this compound (the Compound No.6) is 83.0°–84.0° C. The result of the elemental analysis is: carbon C 83.01 (82.93); hydrogen H 5.78 (5.72); and nitrogen N 3.51 (3.45). The value in parentheses indicates the theoretical value.

Figure 7:
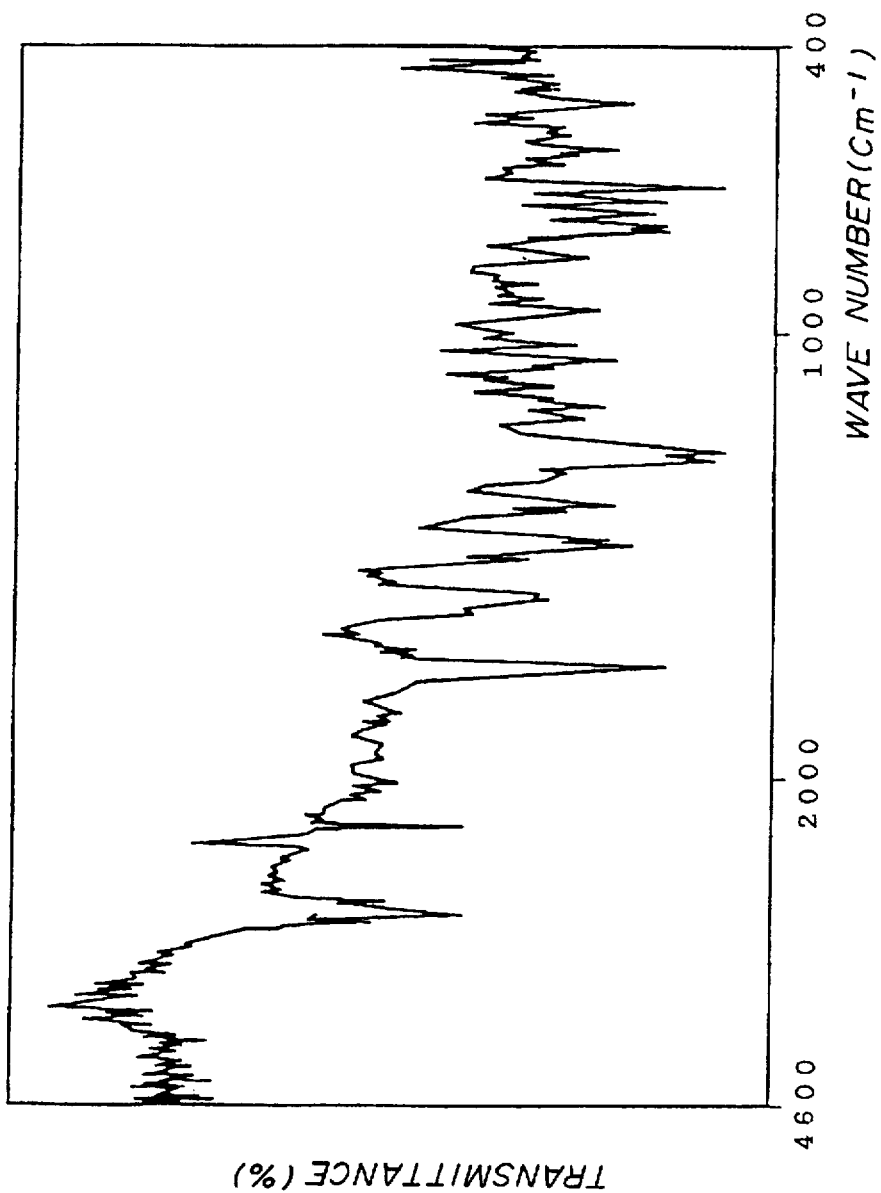
FIG. 7 is a graph showing an infrared absorption spectrum of another 2,3-diphenylindene compound in one embodiment of the present invention.

FIG. 7 shows an infrared absorption spectrum of this 2,3-diphenylindene compound.

Example 1

In order to prepare a medium example (Medium No.1) of the electrophotographic photoconductor, 5 parts by weight of a bisazo dye, 2.5 parts by weight of butyral resin (Denka Butyral Resin #3000-2 from Denki Kagaku Kogyo Co., Ltd.), and 92.5 parts by weight of tetrahydrofuran are dispersed by using a ball mill for 12 hours. The bisazo dye mentioned above consists of a composition represented by formula (IX):

ating layer on the electroconductive support is formed in the same manner as that of the above Example 1 except that a bisazo dye consisting of a composition represented by the following formula (X) is used instead of the bisazo dye represented by the above formula (IX).

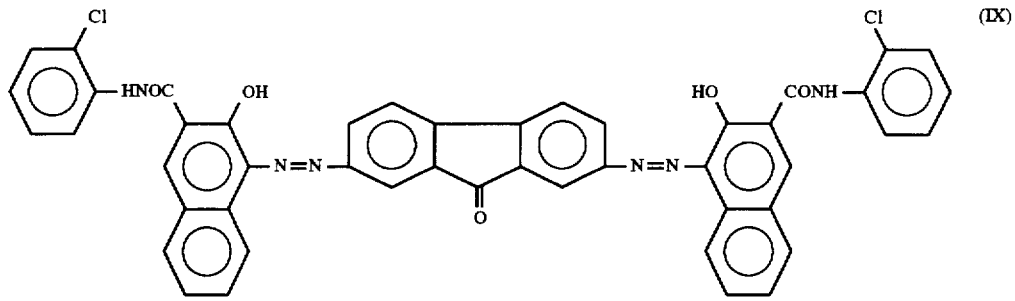

A certain amount of tetrahydrofuran is added so that 2 wt % of the solution is obtained. This solution is coated to a 100-μm thick, aluminum-deposited polyester film by using

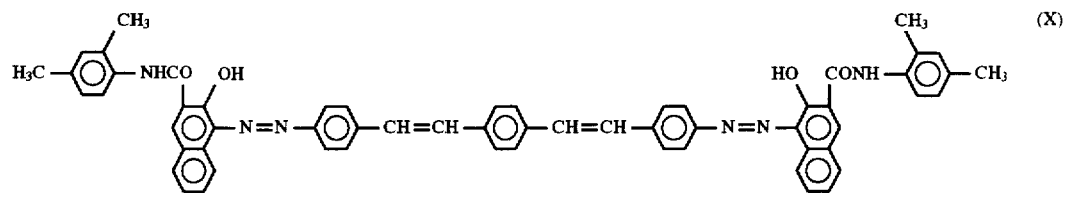

a doctor blade. After dried, a 1.0-μm thick charge generating layer on the support is formed.

In order to form a charge transporting layer on the above-mentioned charge generating layer, 6 parts by weight of the compound example 1 (Compound No.1), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is coated to the charge generating layer by using a doctor blade. After dried, a 20.0-μm thicj charge transporting layer on the charge generating layer is formed. The Example 1 (Medium No.1, Compound No.1) is thus formed, which has a laminated structure including the aluminum electrode, the charge generating layer and the charge transporting layer.

Examples 2–5

Examples 2, 3, 4 and 5 (Medium Nos.2, 3, 4 and 5) are prepared in the same manner as the above Example 1 except that Compound Examples 2, 6, 29 and 40 (Compound Nos.2, 6, 29 and 40) are respectively used instead of a compound example of Compound No.1.

Comparative Example 1 (C/E NO.1)

A comparative example 1 (Medium No.6) is prepared in the same manner as the above Example 1 except that 2,4,7-trinitrofluorenone (TNF) is used instead of the above Compound Example 1.

Example 6

In order to prepare a medium example (Medium No.7) of the electrophotographic photoconductor, the charge gener- In order to form a charge transporting layer on the above charge generating layer, 6 parts by weight of the Compound Example 1 (Compound No.1), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is coated to the above charge generating layer by using a doctor blade. After dried, a 20.0-μm thick charge transporting layer on the charge generating layer is formed. The Example 8 (Medium No.7, Compound No.1) is thus formed, which has a laminated structure including the aluminum electrode, the charge generating layer, and the charge transporting layer.

Examples 7–10

Examples 7, 8, 9 and 10 (Medium Nos.8, 9, 10 and 11) are prepared in the same manner as the above Example 6 except that Compound Examples 2, 6, 29 and 40 (Compound Nos.2, 6, 29 and 40) are respectively used instead of the above Compound Example 1.

Comparative Example 2 (C/E NO.2)

A comparative example 2 (Medium No.12) is prepared in the same manner as the above Example 6 except that 2,4,7-trinitrofluorenone (TNF) is used instead of the above Compound Example 1.

Example 11

In order to prepare a medium example (Medium No.13) of the electrophotographic photoconductor, the charge generating layer on the electroconductive support is formed in the same manner as that of the above Example 1 except that a trisazo dye consisting of a composition represented by the following formula (XI) is used instead of the bisazo dye represented by the above formula (IX).

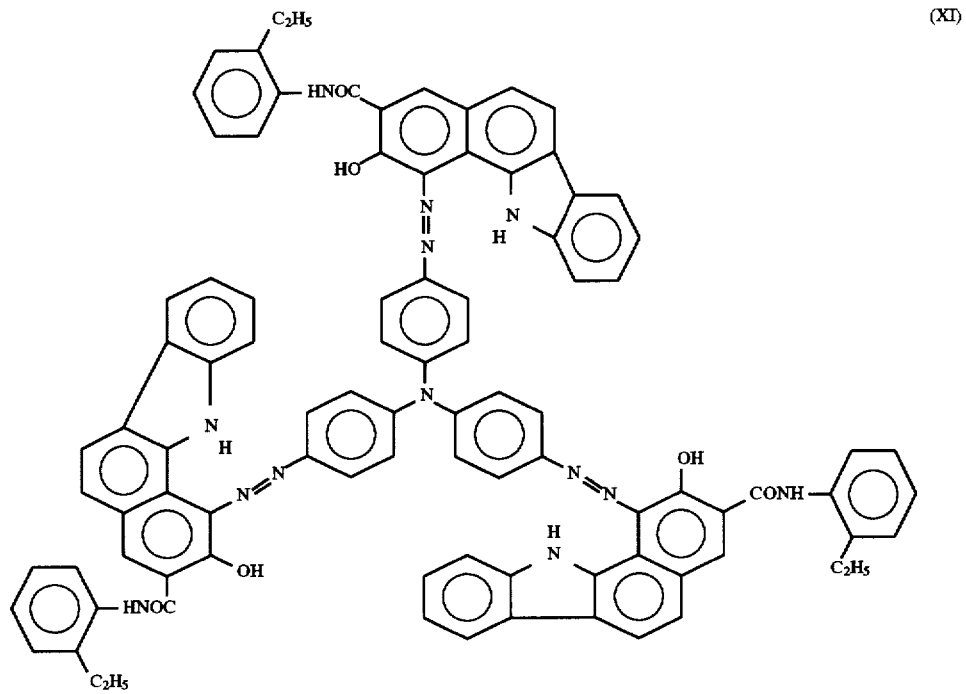

(XI)

In order to form a charge transporting layer on the above charge generating layer, 6 parts by weight of the Compound Example 1 (Compound No.1), 10 parts by weight of polycarbonate resin (K-1300 from Teijin Kasei Co., Ltd.), 0.002 parts by weight of methyl phenyl silicon (KF50-100 cps from Shinetsu Kagaku Kogyo Co., Ltd.), and 94 parts by weight of tetrahydrofuran are solved or dispersed. This solution is coated to the above charge generating layer by using a doctor blade. After dried, a 20.0-μm thick charge transporting layer on the charge generating layer is formed. The Example 11 (Medium No.13, Compound No.1) is thus formed, which has a laminated structure including the aluminum electrode, the charge generating layer, and the charge transporting layer.

Examples 12–15

Examples 12, 13, 14 and 15 (Medium Nos.14, 14, 16 and 27) are prepared in the same manner as the above Example 11 except that the Compound Examples 2, 6, 29 and 40 (Compound Nos.2, 6, 29 and 40) are respectively used instead of the above Compound Example 1.

Comparative Example 3 (C/E NO.3)

A comparative example 3 (Medium No.18) is prepared in the same manner as the above Example 11 except that 2,4,7-trinitrofluorenone (TNF) is used instead of the above Compound Example 1.

Example 16

In order to prepare a medium example (Medium No.19) of the electrophotographic photoconductor, 5 parts by weight of X-type, non-metallic phthalocyanine (Fastogen Blue 812BS from DIC Co., Ltd.), 5 parts by weight of polyvinyl butyral resin (S-Lec BLS from Sekisui Kagaku Co., Ltd.), and 90 parts by weight of tetrahydrofuran are dispersed by using a ball mill for 12 hours. A certain amount of tetrahydrofuran is added so that 2 wt % of the dispersed solution is obtained. This solution is coated to a 100-μm thick, aluminum-deposited polyester film by using a doctor blade. After dried, a 0.5-μm thick charge generating layer on the support is formed.

In order to form a charge transporting layer on the above charge generating layer, 6 parts by weight of the Compound Example 1 (Compound No.1), 10 parts by weight of polycarbonate resin (K-1300 from Teijin Kasei Co., Ltd.), and 94 parts by weight of tetrahydrofuran are solved or dispersed. This solution is coated to the charge generating layer by using a doctor blade. After dried, a 20.0-μm thick charge transporting layer on the charge generating layer is formed. The Example 16 (Medium No.19, Compound No.1) is thus formed, which has a laminated structure including the aluminum electrode, the charge generating layer, and the charge transporting layer.

Examples 17–20

Examples 17, 18, 19 and 20 (Medium Nos.2, 6, 29 and 40) are prepared in the same manner as the above Example 16 except that Compound Examples 2, 6, 29 and 40 (Compound Nos.2, 6, 29 and 40) are respectively used instead of the above Compound Example 1.

Example 21

In order to prepare a medium example (Medium No.24) of the electrophotographic photoconductor, 0.5 g of the bisazo dye represented by the above formula (IX), 10 g of 10-wt % tetrahydrofuran solution of polycarbonate Z (Teijin Kasei Co., Ltd.), and 9 g of tetrahydrofuran are dispersed by using a ball mill. The 10-wt % polycarbonate Z solution, the Compound Example 1, and a positive-hole transporting material, consisting of a composition represented by the following formula (VII), are added so that 2 wt % of the dye, 50 wt % of the polycarbonate Z, 20 wt % of the 2,3-diphenylindene compound, and 28 wt % of the positive-hole transporting material are obtained. This solution is well stirred and coated to a 75-μm thick, aluminium-deposited (1000 Å) polyester film by using a doctor blade. After dried, a 15-μm thick photoconductive layer on the support is formed. The Example 21 (Medium No.24, Compound No.1) is thus formed, wherein the photoconductive layer is a single layer in which the charge generating material and the charge transporting material coexist.

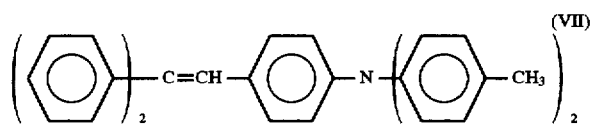

Examples 22–25

Examples 22, 23, 24 and 25 (Medium Nos.25, 26, 27 and 28) are prepared in the same manner as the above Example 21 except that the Compound Examples 2, 6, 29 and 40 (Compound Nos.2, 6, 29 and 40) are respectively used instead of the above Compound Example 1.

Comparative Example 4 (C/E NO.4)

A comparative example 4 (Medium No.29) is prepared in the same manner as the above Example 21 except that no 2,3-diphenylindene compound is used.

Example 26

In order to prepare a medium example (Medium No.30) of the electrophotographic photoconductor, 0.5 g of X-type, non-metallic phthalocyanine (Fastogen Blue 8120 BS from DIC Co., Ltd.), 10 g of 10-wt % tetrahydrofuran solution of polycarbonate Z (Teijin Kasei Co., Ltd.), and 9 g of tetrahydrofuran are dispersed by using a ball mill. The 10-wt % polycarbonate Z solution, the Compound Example 1, and the positive-hole transporting material, consisting of the composition represented by the above formula (VII), are added, so that 2 wt% of the dye, 50 wt % of the polycarbonate Z, 20 wt % of the Compound Example, and 28 wt % of the positive-hole transporting material are obtained. This solution is well stirred and coated to a 75-μm thick, aluminium-deposited (1000 Å) polyester film by using a doctor blade. After dried, a 15-μm thick photoconductive layer on the support is formed. The Example 26 (Medium No.30, Compound No.1) is thus formed, wherein the photoconductive layer is a single layer in which the charge generating material and the charge transporting material coexist.

Examples 27–30

Examples 27, 28, 29 and 30 (Medium Nos.31, 32, 33 and 34) are prepared in the same manner as the above Example 26 except that the Compound Examples 2, 6, 29 and 40 (Compound Nos.2, 6, 29 and 40) are respectively used instead of the above Compound Example 1.

Comparative Example 5 (C/E NO.5)

A comparative example 5 (Medium No.35) is prepared in the same manner as the above Example 26 except that no 2,3-diphenylindene compound is used.

Further, an evaluation test is conducted by using the electrostatic copy analyzer ("SP-428" from Kawaguchi Works Co., Ltd.) to evaluate photosensitive characteristics of the above examples of the electrophotographic photoconductors which are prepared in the manner described above. This evaluation test is performed as follows.

The above examples of the electrophotographic photoconductors are subjected to +6 KV corona charge so that the surfaces of the photoconductors are positively charged. The examples rest on a dark place for 20 seconds. The surface potential Vo (volt) of each example after the resting is measured. After the measurement, light from a tungsten lamp is irradiated to the surface of the example to make the illuminance thereof to be 20 lux, and the quantity $E_{1/2}$ (lux·sec) of the light exposure, needed to change the surface potential from the initial potential Vo to half (Vo/2) of the initial potential, is measured. The results of the above evaluation test for the respective examples are listed in TABLES 41, 42 and 51 which follows.

TABLE 41

| EXAMPLE NO. | MEDIUM NO. | CHARGE GENERATOR | COMPOUND NO | $V_o$ (V) | $E_{1/2}$ (1 ux · sec) |
|---|---|---|---|---|---|
| 1 | 1 | (IX) | 1 | 1580 | 40.1 |
| 2 | 2 | (IX) | 2 | 1600 | 23.6 |
| 3 | 3 | (IX) | 6 | 2170 | 15.8 |
| 4 | 4 | (IX) | 29 | 2030 | 18.9 |
| 5 | 5 | (IX) | 40 | 1980 | 19.3 |
| C/E NO.1 | 6 | (IX) | TNF | 1700 | 72.3 |
| 6 | 7 | (X) | 1 | 1600 | 21.2 |
| 7 | 8 | (X) | 2 | 1510 | 6.8 |
| 8 | 9 | (X) | 6 | 2070 | 6.8 |
| 9 | 10 | (X) | 29 | 1990 | 8.9 |
| 10 | 11 | (X) | 40 | 1900 | 9.3 |
| C/E NO.2 | 12 | (X) | TNF | 1550 | 51.9 |
| 11 | 13 | (XI) | 1 | 1400 | 20.3 |
| 12 | 14 | (XI) | 2 | 1240 | 4.0 |
| 13 | 15 | (XI) | 6 | 1860 | 5.8 |
| 14 | 16 | (XI) | 29 | 1890 | 5.9 |
| 15 | 17 | (XI) | 40 | 1910 | 6.0 |
| C/E NO.3 | 18 | (XI) | TNF | 1500 | 50.1 |

TABLE 42

| EXAMPLE NO. | MEDIUM NO. | CHARGE GENERATOR | COMPOUND NO. | $V_o$ (V) | $E_{1/2}$ (lux · sec) |
|---|---|---|---|---|---|
| 16 | 19 | PHTHALOCYANINE (NON-METAL, X-TYPE) | 1 | 1500 | 10.1 |
| 17 | 20 | PHTHALOCYANINE (NON-METAL, X-TYPE) | 2 | 1420 | 0.7 |
| 18 | 21 | PHTHALOCYANINE (NON-METAL, X-TYPE) | 6 | 1660 | 1.6 |
| 19 | 22 | PHTHALOCYANINE (NON-METAL, X-TYPE) | 29 | 1700 | 1.8 |
| 20 | 23 | PHTHALOCYANINE (NON-METAL, X-TYPE) | 40 | 1650 | 1.9 |

TABLE 51

| EXAMPLE NO. | MEDIUM NO. | CHARGE GENERATOR | COMPOUND NO. | $V_o$ (V) | $E_{1/2}$ (lux · sec) |
|---|---|---|---|---|---|
| 21 | 24 | (IX) | 1 | 1300 | 1.13 |
| 22 | 25 | (IX) | 2 | 1270 | 0.80 |
| 23 | 26 | (IX) | 6 | 1660 | 1.04 |
| 24 | 27 | (IX) | 29 | 1600 | 1.07 |

TABLE 51-continued

| EXAMPLE NO. | MEDIUM NO. | CHARGE GENERATOR | COMPOUND NO. | $V_o$ (V) | $E_{1/2}$ (lux·sec) |
|---|---|---|---|---|---|
| 25 | 28 | (IX) | 40 | 1630 | 1.09 |
| C/E NO. 4 | 29 | (IX) | NONE | 1500 | 1.68 |
| 26 | 30 | PHTHALOCYANINE (NON-METAL, X-TYPE) | 1 | 1250 | 0.96 |
| 27 | 31 | PHTHALOCYANINE (NON-METAL, X-TYPE) | 2 | 1200 | 0.32 |
| 28 | 32 | PHTHALOCYANINE (NON-METAL, X-TYPE) | 6 | 1640 | 0.37 |
| 29 | 33 | PHTHALOCYANINE (NON-METAL, X-TYPE) | 29 | 1620 | 0.39 |
| 30 | 34 | PHTHALOCYANINE (NON-METAL, X-TYPE) | 40 | 1590 | 0.42 |
| C/E NO. 5 | 35 | PHTHALOCYANINE (NON-METAL, X-TYPE) | NONE | 1530 | 1.23 |

As described in the foregoing, the 2,3-diphenylindene compound of the present invention can be produced through a simple, efficient production method. The 2,3-diphenylindene compound of the present invention is readily solved in a binder resin. The 2,3-diphenylindene compound of the present invention has excellent charge acceptance and charge transport abilities, and provides an excellent charge transporting function by including it in the photoconductive layer. The above evaluation test has verified that the electrophotographic photoconductor comprising one 2,3-diphenylindene compound of the present invention provides a good light sensitivity and high durability.

Further, the present invention is not limited to the above-described embodiments, and variations and modifications may be made without departing from the scope of the present invention.

What is claimed is:

1. A cyclopentadiene derivative compound represented by a formula:

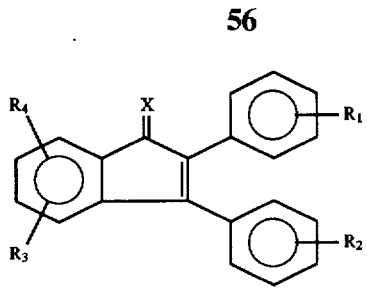

wherein $R_1$, $R_2$, $R_3$, $R_4$ independently represent a hydrogen atom, a halogen atom, a cyano group, a nitro group, or an alkyl group which may have a substituent, wherein X represents:

a substitution group (1) of the formula =C(A)(B) wherein A and B independently represent a halogen atom, a cyano group, an aromatic group which may have a substituent, or a group —$COOR_6$ wherein $R_6$ represents an alkyl group which may have a substituent, or an aromatic group which may have a substituent; or a substitution group (2) of the formula =N—$R_5$ where $R_5$ represents a cyano group, an alkyl group which may have a substituent, or an aromatic group which may have a substituent.

2. The compound according to claim 1, wherein the substituent of said alkyl group of $R_1$ to $R_6$ is halogen or phenyl, the substituent of said aromatic group $R_5$, $R_6$, A and B is chloro, bromo, methyl, ethyl, isopropyl, t-butyl, n-butyl, nitro, cyano, methoxyl, ethoxyl, acetoxyl, methoxycarbonyl, ethocycarbonyl, butoxycarbonyl, methycarbonyl, ethylcarbonyl, N,N-dimethylamino, benzoxyamino N,N-dimethylamido, methylthioxy, trifluoromethyl, or phenyl.

3. The compound according to claim 1, wherein said alkyl group $R_1$ to $R_6$ which may have a substituent is methyl, ethyl, isopropyl, t-butyl, hexyl, octyl, cyclohexyl, cyclopentyl, trifluoromethyl, chloromethyl, bromoethyl, fluoropropyl or benzyl.

4. The compound according to claim 1, wherein said alkyl group $R_1$ to $R_6$ and aromatic group $R_5$, $R_6$, A and B are unsubstituted.

5. The compound according to claim 1, wherein at least one of A and B is cyano.

6. The compound according to claim 1, wherein both A and B are cyano.

* * * * *

UNITED STATES PATENT AND TRADEMARK OFFICE
CERTIFICATE OF CORRECTION

PATENT NO. : 5,750,762
DATED : May 12, 1998
INVENTOR(S) : Megumi Kawahara et al.

It is certified that error appears in the above-identified patent and that said Letters Patent is hereby corrected as shown below:

Title page,
Item [30], Foreign Application Priority Data, should read:
-- Mar. 3, 1994 [JP]   Japan…………………6-33617
   Mar. 10, 1994 [JP]   Japan………………..6-39934 --

Signed and Sealed this

Sixth Day of July, 2004

JON W. DUDAS
*Acting Director of the United States Patent and Trademark Office*